United States Patent
Lovenberg et al.

(10) Patent No.: US 6,239,268 B1
(45) Date of Patent: May 29, 2001

(54) INTERLEUKIN-1 TYPE 3 RECEPTORS

(75) Inventors: Timothy W. Lovenberg, Carlsbad; Tilman Oltersdorf, Cardiff; Chen Wang Liaw, San Diego; William R. Clevenger, Vista; Errol B. DeSouza, Del Mar, all of CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/227,717

(22) Filed: Jan. 8, 1999

Related U.S. Application Data

(63) Continuation of application No. 08/526,704, filed on Sep. 11, 1995, now abandoned, which is a continuation-in-part of application No. 08/303,957, filed on Sep. 9, 1994, now abandoned.

(51) Int. Cl.$^7$ .......................... C07K 14/705; C12N 15/12

(52) U.S. Cl. .................... 536/23.5; 435/69.1; 435/252.3; 435/320.1; 530/350

(58) Field of Search ................................ 435/69.1, 252.3, 435/320.1; 536/23.5; 530/350

(56) References Cited

U.S. PATENT DOCUMENTS

| | | | |
|---|---|---|---|
| 4,968,607 | 11/1990 | Dower et al. | 435/69.1 |
| 5,081,228 | 1/1992 | Dower et al. | 530/35.1 |
| 5,180,812 | 1/1993 | Dower et al. | 530/351 |
| 5,319,071 | 6/1994 | Dower et al. | 530/350 |

FOREIGN PATENT DOCUMENTS

| | | |
|---|---|---|
| 623 674 A1 | 11/1994 | (EP) . |
| WO 93/07863 | 4/1993 | (WO) . |
| WO 93/19777 | 10/1993 | (WO) . |
| WO 94/20517 | 9/1994 | (WO) . |

OTHER PUBLICATIONS

Takao et al., "Species differences in [$^{125}$I]interleukin–1 binding in brain, endocrine and immune tissues," *Brain Research 623:* 172–176, 1993.
Hart et al., "An mRNA homologous to interleukin–1 receptor type–I is expressed in cultured rat sympathetic ganglia," *Journal of Neuroimmunology 44:* 49–56, 1993.
Ericsson et al., "Distribution of the Type I Interleukin–1 Receptor mRNA in the Central Nervous System of the Rat," *Society of Neuroscience Abstracts 19:* 95, 1993.
Liu et al., "A Soluble IL–1 Receptor Is Expressed in Cultured Rat Sympathetic Ganglia from the Type I IL–1 Receptor Gene," *Society of Neuroscience Abstracts 19:* 95, 1993.
Takao et al., "Reciprocal Modulation of Interleukin–1β (IL–1β) and IL–1 Receptors by Lipopolysaccharide (Endotoxin) Treatment in the Mouse Brain–Endocrine–Immune Axis," *Endocrinology 132*(4): 1497–1504, 1993.

Takao et al., "Type I interleukin–1 receptors in the mouse brain–endocrine–immune axis labelled with [$^{125}$]recombinant human interleukin–1 receptor antagonist," *Journal of Neuroimmunology 41:* 51–60, 1992.
Hart et al., "Interleukin–1 Receptor mRNA Is Induced in Cultured Rat Sympathetic Ganglia," *Society of Neuroscience Abstracts 18:* 1298, 1992.
Cunningham, Jr. et al., "In situ Histochemical Localization of Type I Interleukin–1 Receptor Messenger RNA in the Central Nervous System, Pituitary, and Adrenal Gland of the Mouse," *Journal of Neuroscience 12*(3): 1101–1114, 1992.
Cunningham, Jr. et al., "Localization of Interleukin–1 Receptor Messenger RNA in Murine Hippocampus," *Endocrinology 128*(5): 2666–2668, 1991.
Takao et al., "Interleukin–1 Receptors in Mouse Kindey: Identification, Localization, and Modulation by Lipopolysaccharide Treatment," *Endocrinology 128*(5): 2618–2624, 1991.
Takao et al., "Interleukin–1 Receptors in Mouse Brain: Characterization and Neuronal Localization," *Endocrinology 127*(6): 3070–3078, 1990.
Takao et al., "Identification of Interleukin–1 Receptors in Mouse Testis," *Endocrinology 127*(1): 251–258, 1990.
Bomsztyk et al., "Evidence for different interleukin 1 receptors in murine B–and T–cell lines," *Proc. Natl. Acad. Sci. USA 86:* 8034–8038, 1989.
Chizzonite et al., "Two high–affinity interleukin 1 receptors represent separate gene products," *Proc. Natl. Acad. Sci. USA 86:* 8029–8033, 1989.
Dinarello, "Biology of interleukin 1," *FASEB Journal 2:* 108–115, 1988.
Dinarello et al., "Interleukin–1 and Interleukin–1 Antagonism," *Blood 77*(8): 1627–1652, 1991.
Horuk et al., "A Biochemical and Kinetic Analysis of the Interleukin–1 Receptor. Evidence for Differences in Molecular Properties of IL–1 Receptors," *Journal of Biological Chemistry 262:* 16275–16278, 1987.
Horuk and McCubrey, "The interleukin–1 receptor in Raji human B–lymphoma cells. Molecular characterization and evidence for receptor–mediated activation of gene expression," *Biochem. Journal 260:* 657–663, 1989.
Kluger, "Fever: Role of Pyrogens and Cryogens," *Physiological Reviews 71*(19): 93–127, 1991.
McCarthy et al., "Suppression of food intake during infection: is interleukin–1 involved?," *American Journal of Clinical Nutrition 42:* 1179–1182, 1985.
Mizel, "The interleukins," *FASEB Journal 3:* 2379–2388, 1989.

(List continued on next page.)

Primary Examiner—John Ulm
(74) *Attorney, Agent, or Firm*—Seed Intellectual Property Law Group PLLC

(57) ABSTRACT

The present invention provides isolated nucleic acid molecules encoding soluble and membrane bound forms of Interleukin-1 Type 3 receptors, as well as recombinant expression vectors and host cells suitable for expressing such receptors.

13 Claims, 4 Drawing Sheets

OTHER PUBLICATIONS

Opp et al., "Interleukin 1 alters rat sleep: temporal and dose-related effects," *American Journal of Physiol. 260:* R52–R58, 1991.

Oppenheim et al., "There is more than one interleukin 1," *Immunology Today 7*(2): 45–46, 1986.

Rivier and Vale, "In the Rat, Interleukin–1α Acts at the Level of the Brain and Gonads to Interfere with Gonadotropin and Sex Steroid Secretion," *Endocrinology 124*(5): 2105–2109, 1989.

Woolski et al., "Corticotropin–Releasing Activity of Monokines," *Science 230:* 1035–1037, 1985.

HOMOLOGY OF THE HUMAN IL-1 TYPE 3 RECEPTOR WITH
RELATED RECEPTORS

|  |  | OVERALL | EXTRACELLULAR | INTRACELLULAR | MEMBRANE |
|---|---|---|---|---|---|
| RAT | IL-1 R3 | 66 | 63 | 70 | 66 |
| HUMAN | IL-1 R1 | 42 | 34 | 55 | 60 |
| RAT | IL-1 R1 | 40 | 34 | 52 | 60 |
| MOUSE | IL-1 R1 | 40 |  |  |  |
| HUMAN | IL-1 R2 | 23 |  |  |  |
| MOUSE | IL-1 R2 | 23 |  |  |  |
| MOUSE | ST-2L | 29 |  |  |  |

INTERLEUKIN-1 TYPE 3 RECEPTORS

CROSS-REFERENCE TO RELATED APPLICATIONS

This application is a continuation of U.S. patent application Ser. No. 08/526,704, filed Sep. 11, 1995, now abandoned, which application is a continuation-in-part of U.S. application Ser. No. 08/303,957, filed Sep. 9, 1994 now abandoned.

TECHNICAL FIELD

The present invention relates generally to cell surface receptors, and more specifically, to Interleukin-1 Type 3 receptors.

BACKGROUND OF THE INVENTION

Interleukin-1 ("IL-1") is a cytokine which is known to be a key mediator of immunological and pathological responses to stress, infection and antigenic challenge (Oppenheim et al., *Immunol. Today* 7:45–46, 1986; Dinarello, *FASEB J.* 2:108–115, 1988; and Mizel, *FASEB J.* 3:2379–2388, 1989). In addition, IL-1 is known to have a variety of effects on the brain and central nervous system. For example, IL-1 has been postulated to be involved in the induction of fever (Kluger, *Physiol. Rev.* 71:93–127, 1991), increased duration of slow wave sleep (Opp et al., *Am. J. Physiol.* 260:R52–R58, 1991), decreased appetite (McCarthy et al., *Am. J. Clin. Nutr.* 42:1179–1182, 1985), activation of the hypothalamic-pituitary-adrenal ("HPA") axis (Woloski et al., *Science* 230:1035–1037, 1985), and inhibition of the hypothalamic-pituitary-gonadal axis (River and Vale, *Endocrinology* 124:2105–2109, 1989).

In light of the above-noted effects of IL-1 (as well as many others), substantial effort has been undertaken in order to identify receptors for IL-1. Briefly, at least two types of receptors are known to be expressed on the surface of certain immune cells in both human and murine derived lines. Type I receptors bind both IL-1α and IL-1β, and can be found on T cells, fibroblasts, keratinocytes, endothelial cells, synovial lining cells, chondrocytes and hepatocytes (U.S. Pat. Nos. 4,968,607, 5,081,228, and 5,180,812; Chizzonite et al., *PNAS* 86:8029–8033, 1989; Dinarello et al., *Blood* 77:1627–1652, 1991). Type II receptors can be found on various B cell lines, including the Raji human B-cell lymphoma line (Bomsztyk et al., *PNAS* 86:8034–8038, 1989; Horuk et al., *J. Biol. Chem.* 262:16275–16278, 1987; Horuk and McCubrey, *Biochem. J.* 260:657–663, 1989).

The present invention provides new, previously unidentified Interleukin receptors, designated Interleukin-1 Type 3 receptors ("IL-1-3R"). In addition, the present invention provides compositions and methods which utilize such receptors, as well as other, related advantages.

SUMMARY OF THE INVENTION

Briefly stated, the present invention provides compositions and methods which comprise Interleukin-1 Type 3 receptors. Within one aspect of the present invention isolated nucleic acid molecules are provided which encode Interleukin-1 Type 3 receptors. Within one embodiment, the isolated nucleic acid molecules comprise the sequence of nucleotides in Sequence I.D. No. 1, from nucleotide number 129 to nucleotide number 1814. Within another embodiment, the isolated nucleic acid molecules encode a protein having the amino acid sequence of Sequence I.D. No. 2, from amino acid number 1 to amino acid number 562. Within other embodiments, isolated nucleic acid molecules are provided in Sequence I.D. No. 3, from nucleotide number 89 to nucleotide number 1771. Within another embodiment, the nucleic acid molecules encode a protein having the amino acid sequence of Sequence I.D. No. 4, from amino acid number 1 to amino acid number 561. Nucleic acid molecules which encode IL-1 Type 3 receptors of the present invention may be isolated from virtually any warm-blooded animal, including for example, humans, macaques, horses, cattle, sheep, pigs, dogs, cats, rats and mice.

Within related aspects of the present invention, isolated nucleic acid molecules are provided which encode soluble Interleukin-1 Type 3 receptors. Within one embodiment, the isolated nucleic acid molecules comprise the sequence of nucleotides in Sequence I.D. No. 1, from nucleotide number 129 to nucleotide number 1136. Within other embodiments, the isolated nucleic acid molecules encode a protein having the amino acid sequence of Sequence I.D. No. 2, from amino acid number 1 to amino acid number 336. Within another embodiment, the nucleic acid molecules comprise the sequence of nucleotides in Sequence I.D. No. 3, from nucleotide number 89 to nucleotide number 1102. Within yet another embodiment, the nucleic acid molecules encode a protein having the amino acid sequence of Sequence I.D. No. 4, from amino acid number 1 to amino acid number 338. As above, nucleic acid molecules which encode soluble IL-1 Type 3 receptors of the present invention may be isolated from virtually any warm-blooded animal, including for example, humans, macaques, horses, cattle, sheep, pigs, dogs, cats, rats and mice.

Within other aspects of the present invention, expression vectors are provided which are capable of expressing the above-described nucleic acid molecules. Within one embodiment, such vectors comprise a promoter operably linked to one of the above-described nucleic acid molecules. Within other embodiments, recombinant viral vectors are provided which are capable of directing the expression of one of the above described nucleic acid molecules. Representative examples of such viral vectors include retroviral vectors, adenoviral vectors, and herpes simplex virus vectors. Also provided by the present invention are host cells containing one of the above-described recombinant vectors.

Within other aspects of the present invention, isolated Interleukin-1 Type 3 receptors are provided. Within one embodiment, such receptors have the amino acid sequence of Sequence I.D. No. 2, from amino acid number 1 to amino acid number 562. Within another embodiment, the receptors have the sequence of Sequence I.D. No. 4, from amino acid number 1 to amino acid number 561. Within yet further aspects of the invention, isolated soluble Interleukin-1 Type 3 receptors are provided. Within one embodiment, the isolated soluble Interleukin-1 Type 3 receptors have the amino acid sequence of Sequence I.D. No. 2, from amino acid number 1 to amino acid number 336. Within another embodiment, the soluble receptors have the sequence of Sequence I.D. No. 4, from amino acid number 1 to amino acid number 338.

Within other aspects of the invention, isolated antibodies capable of specifically binding to an Interleukin-1 Type 3 receptor are provided. Within one embodiment, the antibody may be selected from the group consisting of polyclonal antibodies, monoclonal antibodies, and antibody fragments. Within other embodiments, antibodies are provided which are capable of blocking the binding of IL-1 to an Interleukin-1 Type 3 receptor. Within preferred embodiments, the antibody is selected from the group consisting of murine and human antibodies. In addition to antibodies, the present invention also provides hybridomas which produces an antibody as described above.

Within yet another aspect of the present invention, nucleic acid molecules are provided which are capable of specifically hybridizing to a nucleic acid molecule encoding any of the Interleukin-1 Type 3 receptors described above. Such molecules may be between at least "y" nucleotides long, wherein "y" is any integer between 14 and 2044, and furthermore, may be selected suitable for use as probes or primers described below. Particularly preferred probes of the present invention are at least 18 nucleotides in length.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

DETAILED DESCRIPTION OF THE INVENTION

Definitions

Figure 1:
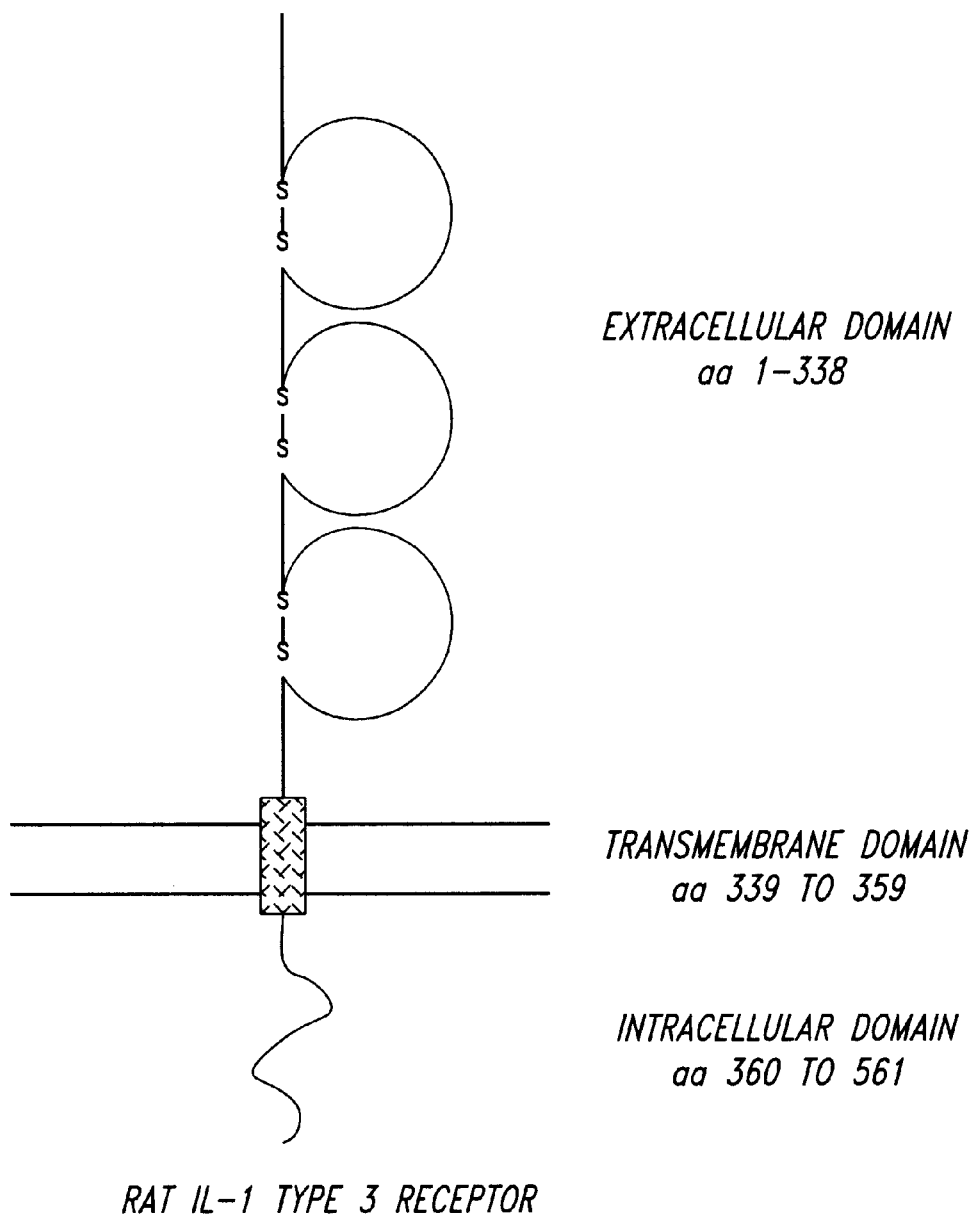
FIG. 1 schematically illustrates a rat IL-1 type 3 receptor.

Prior to setting forth the invention, it may be helpful to an understanding thereof to set forth definitions of certain terms to be used hereinafter.

"Interleukin-1 Type 3 Receptors" ("IL-1-3R") refers to receptor proteins which bind Interleukin-1 (α or β), and, when expressed on a cell surface, transduce the signal provided by Interleukin-1 to the cell, thereby mediating a biological effect within the cell. In their native configuration, IL-1 Type 3 receptors exist as membrane bound proteins, consisting of an extracellular domain, transmembrane domain, and intracellular domain (see FIG. 1). IL-1-3R may be distinguished from other Interleukin-1 receptors based upon criteria such as affinity of substrate binding, tissue distribution, and sequence homology. For example, IL-1-3R of the present invention should be greater than 50% homologous, preferably greater than 75% to 80% homologous, more preferably greater than 85% to 90% homologous, and most preferably greater than 92%, 95%, or 97% homologous to the IL-1-3R disclosed herein (e.g., Sequence I.D. No. 1). As utilized within the context of the present invention, IL1-3R should be understood to include not only the proteins which are disclosed herein, but substantially similar derivatives and analogs as discussed below.

"Soluble Interleukin-1 Type 3 Receptor" ("sIL1-3R") refers to a protein which has an amino acid sequence corresponding to the extracellular region of an Interleukin-1 Type 3 receptor. The extracellular region of IL-1-3R may be readily determined by a hydrophobicity analysis utilizing a computer program such as PROTEAN (DNASTAR, Madison, Wis.), or by an alignment analysis with other known type 1 and type 2 Interleukin-1 receptors.

"Nucleic acid molecule" refers to a nucleic acid polymer or nucleic acid sequence, which exists in the form of a separate fragment or as a component of a larger nucleic acid construct. The nucleic acid molecule must have been derived from nucleic acids isolated at least once in substantially pure form, (i.e., substantially free of contaminating endogenous materials), and in a quantity or concentration enabling identification and recovery. Such sequences are preferably provided in the form of an open reading frame uninterrupted by internal nontranslated sequences, or introns. As utilized herein, nucleic acid molecules should be understood to include deoxyribonucleic acid ("DNA") molecules (including genomic and cDNA molecules), ribonucleic acid ("RNA") molecules, hybrid or chimeric nucleic acid molecules (e.g., DNA-RNA hybrids), and where appropriate, nucleic acid molecule analogs and derivatives (e.g., peptide nucleic acids ("PNA")). Nucleic acid molecules of the present invention may also comprise sequences of non-translated nucleic acids where such additional sequences do not interfere with manipulation or expression of the open reading frame (e.g., sequences which are 5' or 3' from the open reading frame).

"Recombinant expression vector" refers to a replicable nucleic acid construct used either to amplify or to express nucleic acid sequences which encode IL-1 Type 3, or sIL-1 Type 3 receptors. This construct comprises an assembly of (1) a genetic element or elements having a regulatory role in gene expression, for example, promoters, and (2) the structural or coding sequence of interest. The recombinant expression vector may also comprise appropriate transcription and translation initiation and termination sequences.

As noted above, the present invention provides isolated nucleic acid molecules encoding Interleukin-1 Type 3 receptors. One representative IL-1 Type 3 receptor which may be obtained utilizing the methods described herein (see, e.g., Example 1) is schematically illustrated in FIG. 1. Briefly, this IL-1 Type 3 receptor (see Sequence I.D. Nos. 1 and 2) is composed of an Extracellular N-terminal Domain (amino acids 1–336), a Transmembrane Domain (amino acids 337–357), and a C-terminal Intracellular Domain (358–562).

Although the above IL-1 Type 3 receptor has been provided for purposes of illustration (see also Sequence I.D. Nos. 3 and 4), the present invention should not be so limited. In particular, "IL-1-3R" and "sIL-1-3R" as utilized herein should be understood to include a wide variety of IL-1 Type 3 receptors which are encoded by nucleic acid molecules that have substantial similarity to the sequences disclosed in Sequences I.D. Nos. 1 and 3. As utilized within the context of the present invention, nucleic acid molecules which encode IL-1 Type 3 receptors are deemed to be substantially similar to those disclosed herein if: (a) the nucleic acid sequence is derived from the coding region of a native IL-1 Type 3 receptor gene (including, for example, allelic variations of the sequences disclosed herein); (b) the nucleic acid sequence is capable of hybridization to nucleic acid sequences of the present invention under conditions of either moderate (e.g., 50% formamide, 5×SSPE, 5×Denhardt's, 0.1% SDS, 100 ug/ml Salmon Sperm DNA, and a temperature of 42° C.) or high stringency (see Sambrook et al., *Molecular Cloning: A Laboratory Manual,* 2d Ed., Cold Spring Harbor Laboratory Press, NY, 1989); or (c) nucleic acid sequences are degenerate as a result of the genetic code to the nucleic acid sequences defined in (a) or (b). Furthermore, as noted above, although DNA molecules are primarily referred to herein, as should be evident to one of skill in the art given the disclosure provided herein, a wide variety of related nucleic acid molecules may also be utilized in various embodiments described herein, including for example, RNA, nucleic acid analogues, as well as chimeric nucleic acid molecules which may be composed of more than one type of nucleic acid.

In addition, as noted above, within the context of the present invention "IL-1 Type 3 receptors" and "soluble IL-1 Type 3 receptors" should be understood to include derivatives and analogs of the IL-1 Type 3 receptors described above. Such derivatives include allelic variants and genetically engineered variants that contain conservative amino acid substitutions and/or minor additions, substitutions or deletions of amino acids, the net effect of which does not substantally change the biological activity (e.g., signal transduction) or function of the IL-1 Type 3 receptor. Such derivatives are generally greater than about 50% homologous, preferably greater than 75% to 80% homologous, more preferably greater than 85% to 90% homologous, and most preferably greater than 92%, 95% or 97% homologous. Homology may be determined, for example, by comparing sequence information using the GAP computer program, version 6.0, available from the University of Wisconsin Genetics Computer Group (UWGCG).

The primary amino acid structure of IL-1 Type 3 receptors may also be modified by derivatizing amino acid side chains, and/or the amino or carboxy termus with various functional groups, in order to allow for the formation of various conjugates (e.g., protein-IL-1-3R conjugates). Alternatively, conjugates of IL-1-3R (and sIL-1-3R) may be constructed by recombinantly producing fusion proteins. Such fusion proteins may comprise, for example, IL-1-3R-protein Z wherein protein Z is another cytokine receptor (e.g., IL-2R, IL-3R, IL-4R, IL-5R, IL-6R, IL-7R, IL-8R, IL-9R, IL-10R, IL-11R, IL-12R, IL-13R, IL-14R, IL-15R or TNF ($\alpha$ or $\beta$) receptor; see WO91/03553); a binding portion of an antibody; a toxin (as discussed below); or a protein or peptide which facilitates purification or identification of IL-1-3R (e.g., poly-His). For example, a fusion protein such as human IL-1-3R $(His)_n$ or sIL-1-3R $(His)_n$ may be constructed in order to allow purification of the protein via the poly-His residue, for example, on a NTA nickel-chelating column. The amino acid sequence of a IL-1 Type 3 receptor may also be linked to the peptide Asp-Tyr-Lys-Asp-Asp-Asp-Asp-Lys (DYKDDDDK) (Sequence I.D. No. 5) (Hopp et al., *Bio/Technology* 6:1204, 1988) in order to facilitate purification of expressed recombinant protein.

The present invention also includes IL-1-3R (and sIL-1-3R) proteins which may be produced either with or without associated native-pattern glycosylation. For example, expression of IL-1-3R DNAs in bacteria such as *E. coli* provides non-glycosylated molecules. In contrast, IL-1-3R expressed in yeast or mammalian expression systems (as discussed below) may vary in both glycosylation pattern and molecular weight from native IL-1-3R, depending on the amino acid sequence and expression system which is utilized. In addition, functional mutants of mammalian IL-1-3R having inactivated glycosylation sites may also be produced in a homogeneous, reduced-carbohydrate form, utilizing oligonucleotide synthesis, site-directed mutagenesis, or random mutagenesis techniques. Briefly, N-glycosylation sites in eukaryotic proteins are generally characterized by the amino acid triplet Asn-$A_1$-Z, where $A_1$ is any amino acid except Pro, and Z is Ser or Thr. In this triplet, asparagine provides a side chain amino group for covalent attachment of carbohydrate. Such sites may be eliminated by deleting Asn or Z, substituting another amino acid for Asn or for residue Z, or inserting a non-Z amino acid between $A_1$ and Z, or an amino acid other than Asn between Asn and $A_1$.

Proteins which are substantially similar to IL-1-3R proteins may also be constructed by, for example, substituting or deleting various amino acid residues which are not required for biological activity. For example, cysteine residues may be deleted or replaced with other amino acids to prevent formation of incorrect intramolecular disulfide bridges upon renaturation. Similarly, adjacent dibasic amino acid residues may be modified for expression in yeast systems in which KEX2 protease activity is present.

Not all mutations in the nucleotide sequence which encodes IL-1-3R will be expressed in the final product. For example, nucleotide substitutions may be made in order to avoid secondary structure loops in the transcribed mRNA, or to provide codons that are more readily translated by the selected host, and thereby enhance expression within a selected host.

Generally, substitutions at the amino acid level should be made conservatively, i.e., the most preferred substitute amino acids are those which have characteristics resembling those of the residue to be replaced. When a substitution, deletion, or insertion strategy is adopted, the potential effect of the deletion or insertion on biological activity should be considered utilizing, for example, the signalling assay disclosed within the Examples.

Mutations which are made to the sequence of the nucleic acid molecules of the present invention should generally preserve the reading frame phase of the coding sequences. Furthermore, the mutations should preferably not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon, and the expressed IL-1-3R mutants screened for the biological activity. Representative methods for random mutagenesis include those described by Ladner et al. in U.S. Pat. Nos. 5,096,815; 5,198,346; and 5,223,409.

As noted above, mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, site-directed mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik, *Bio Techniques*, January 1985, 12–19); Smith et al. (*Genetic Engineering: Principles and Methods*, Plenum Press, 1981); Sambrook et al. (*Molecular cloning: A Laboratory Manual*, 2d Ed., Cold Spring Harbor Laboratory Press, 1989); and U.S. Pat. Nos. 4,518,584 and 4,737,462, which are incorporated by reference herein.

IL-1 Type 3 receptors, as well as substantially similar derivatives or analogs may be used as therapeutic reagents, immunogens, reagents in receptor-based immunoassays, or as binding agents for affinity purification procedures.

Moreover, IL-1 Type 3 receptors of the present invention may be utilized to screen compounds for IL-1 Type 3 receptor agonist or antagonistic activity. IL-1 Type 3 receptor proteins may also be covalently bound through reactive side groups to various insoluble substrates, such as cyanogen bromine-activated, bisoxirane-activated, carbonyldiimidazole-activated, or tosyl-activated, agarose structures, or by adsorbing to polyolefin surfaces (with or without glutaraldehyde cross-linking). Once bound to a substrate, IL-1-3R may be used to selectively bind (for purposes of assay or purification) anti-IL-1-3R antibodies or IL-1.

Isolation of IL-1 Type 3 Receptor cDNA Clones

As noted above, the present invention provides isolated nucleic acid molecules which encode IL-1 Type 3 receptors. Briefly, nucleic acid molecules which encode IL-1 Type 3 receptors of the present invention may be readily isolated from a variety of warm-blooded animals, including for example, humans, macaques, horses, cattle, sheep, pigs, dogs, cats, rats and mice. Particularly preferred tissues from which nucleic acid molecules which encode IL-1 Type 3 receptors may be isolated include brain, kidney and lung. Nucleic acid molecules which encode IL-1 Type 3 receptors of the present invention may be readily isolated from conventionally prepared cDNA libraries (see, e.g., Sambrook et al., *Molecular Cloning: A Laboratory Manual*, 2d Ed., Cold Spring Harbor Laboratory Press, NY, 1989) or from commercially obtained libraries (e.g., Stratagene, LaJolla, Calif.) utilizing the disclosure provided herein. Particularly preferred methods for obtaining isolated DNA molecules which encode IL-1 Type 3 receptors of the present invention are described in more detail below in Example 1 (see also Sequence I.D. Nos. 1 and 3).

As noted above, within particularly preferred embodiments of the invention, isolated nucleic acid molecules are provided which encode human IL-1 Type 3 receptors. Briefly, such nucleic acid molecules may be readily obtained by probing a human cDNA library either with a specific sequence as described below in Example 1, or with a rat sequence (e.g., Sequence I.D. Nos. 2 or 4) under conditions of high stringency (e.g., 50% formamide, 5×SSC, 5×Denharts, 0.1% SDS, 100 ug/ml salmon sperm DNA, at 42° C. for 12 hours). This may be followed by extensive washing with 2×SSC containing 0.2% SDS at 50° C. Suitable cDNA libraries may be obtained from commercial sources (e.g., Stratagene, LaJolla, Calif.; or Clontech, Palo Alto, Calif., or prepared utilizing standard techniques (see, e.g,. Sambrook et al., supra).

Production of Recombinant IL-1 Type 3 Receptors

As noted above, the present invention also provides recombinant expression vectors which include synthetic or cDNA-derived DNA fragments encoding IL-1 Type 3 receptors or substantially similar proteins, which are operably linked to suitable transcriptional or translation regulatory elements derived from mammalian, microbial, viral or insect genes. Such regulatory elements include a transcriptional promoter, an optional operator sequence to control transcription, a sequence encoding suitable mRNA ribosomal binding sites, and, within preferred embodiments, sequences which control the termination of transcription and translation. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

Expression vectors may also contain DNA sequences necessary to direct the secretion of a polypeptide of interest. Such DNA sequences may include at least one secretory signal sequence. Representative secretory signals include the alpha factor signal sequence (pre-pro sequence; Kurjan and Herskowitz, *Cell* 30:933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3:439–447, 1983), the α-1-antitrypsin signal sequence (Kurachi et al., *Proc. Natl. Acad Sci. USA* 78:6826–6830, 1981), the β-2 plasmin inhibitor signal sequence (Tone et al., *J. Biochem.* (Tokyo) 102:1033–1042, 1987), the tissue plasminogen activator signal sequence (Pennica et al., *Nature* 301:214–221, 1983), the *E. coli* PhoA signal sequence (Yuan et al., *J. Biol. Chem.* 265:13528–13552, 1990) or any of the bacterial signal sequences reviewed, for example, by Oliver (*Ann. Rev. Microbiol.* 39:615–649, 1985). Alternatively, a secretory signal sequence may be synthesized according to the rules established, for example, by von Heinje (*Eur. J. Biochem.* 133:17–21, 1983; *J. Mol. Biol.* 184:99–105, 1985; *Nuc. Acids Res.* 14:4683–4690, 1986).

For expression, a nucleic acid molecule encoding a IL-1 Type 3 receptor is inserted into a suitable expression vector, which in turn is used to transform or transfect appropriate host cells for expression. Host cells for use in practicing the present invention include mammalian, avian, plant, insect, bacterial and fungal cells. Preferred eukaryotic cells include cultured mammalian cell lines (e.g., rodent or human cell lines) and fungal cells, including species of yeast (e.g., Saccharomyces spp., particularly *S. cerevisiae*, Schizosaccharomyces spp., or Kluyveromyces spp.) or filamentous fungi (e.g., Aspergillus spp., Neurospora spp.). Strains of the yeast *Saccharomyces cerevisiae* are particularly preferred. Methods for producing recombinant proteins in a variety of prokaryotic and eukaryotic host cells are generally known in the art (see "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.) Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences which must be transfected into the host cell may be minimized and overall yield of biologically active protein may be maximized.

Suitable yeast vectors for use in the present invention include YRp7 (Struhl et al., *Proc. Natl. Acad Sci. USA* 76:1035–1039, 1978), YEp13 (Broach et al., *Gene* 8:121–133, 1979), POT vectors (Kawasaki et al., U.S. Pat. No. 4,931,373, which is incorporated by reference herein), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid), URA3 (Botstein et al., *Gene* 8:17, 1979), HIS3 (Struhl et al., ibid.) or POT1 (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982; Kawasaki, U.S. Pat. No. 4,599,311) or alcohol dehydrogenase genes (Young et al., in *Genetic Engineering of Microorganisms for Chemicals*, Hollaender et al. (eds.), p. 355, Plenum, New York, 19822; Ammerer, *Meth. Enzymol* 101:192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304:652–654, 1983; Irani and Kilgore, U.S. patent application Ser. No. 07/784,653, which is incorporated herein by reference). The expression units may also include a transcriptional terminator, such as the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4:2093–2099, 1985) and the tpiA promoter. An example of a suitable terminator is the ADH3 terminator (McKnight et al., ibid., 1985). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell will generally contain a genetic defect that is complemented by the selectable marker present on the expression vector. Choice of a particular host and selectable marker is well within the level of ordinary skill in the art. To optimize production of the heterologous proteins in yeast, for example, it is preferred that the host strain carries a mutation, such as the yeast pep4 mutation (Jones, *Genetics* 85:23–33, 1977), which results in reduced proteolytic activity.

In addition to fungal cells, cultured mammalian cells may be used as host cells within the present invention. Preferred cultured mammalian cells for use in the present invention include the COS-1 (ATCC No. CRL 1650), COS-7 (ATCC No. CRL 1651), BHK (ATCC No. CRL 1632), and 293 (ATCC No. CRL 1573; Graham et al., *J. Gen. Virol.* 36:59–72, 1977) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), Ltk$^-$ (ATCC) No. CCL 1.3) and RINm 5AHT$_2$B (Orskov and Nielson, *FEBS* 229(1):175–178, 1988).

Mammalian expression vectors for use in carrying out the present invention should include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-1 promoter (Palmiter et al., U.S. Pat. No. 4,579,821), a mouse V$_j$ promoter (Bergman et al., *Proc. Natl. Acad. Sci. USA* 81:7041–7045, 1983; Grant et al., *Nuc. Acids Res.* 15:5496, 1987) and a mouse V$_H$ promoter (Loh et al., *Cell* 33:85–93, 1983). A particularly preferred promoter is the major late promoter from Adenovirus 2 (Kaufman and Sharp, *Mol. Cell. Biol.* 2:1304–13199, 1982). Such expression vectors may also contain a set of RNA splice sites located downstream from the promoter and upstream from the DNA sequence encoding the peptide or protein of interest. Preferred RNA splice sites may be obtained from SV40, adenovirus and/or immunoglobulin genes. Alternatively, within certain embodiments RNA splice sites may be located downstream from the DNA sequence encoding the peptide or protein of interest. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse 1 enhancer (Gillies, *Cell* 33:717–728, 1983). Expression vectors may also include sequences encoding the adenovirus VA RNAs. Suitable vectors can be obtained from commercial sources (e.g., Invitrogen, San Diego, Calif.; Stratagene, La Jolla, Calif.).

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., NY, 1987), which are incorporated herein by reference. To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate vector at the same time as the IL-1 Type 3 receptor sequence, or they may be introduced on the same vector. If on the same vector, the selectable marker and the IL-1 Type 3 receptor sequence may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells which satisfy these criteria may then be cloned and scaled up for production.

Preferred prokaryotic host cells for use in carrying out the present invention are strains of the bacteria *Escherichia coli*, although Bacillus and other genera are also useful. Techniques for transforming these hosts and expressing foreign DNA sequences cloned therein are well known in the art (see, e.g., Maniatis et al., *Molecular Cloning: A Laboratory Manual*, Cold Spring Harbor Laboratory, 1982; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101: 155–164, 1983), lac (Casadaban et al., *J. Bacteriol.* 143:971–980, 1980), and phage k (Queen, *J. Mol. Appl. Genet.* 2:1–10, 1983) promoter systems. Plasmids useful for transforming bacteria include pBR322 (Bolivar et al., *Gene* 2:95–113, 1977), the pUC plasmids (Messing, *Meth. Enzymol.* 101:20–78, 1983; Vieira and Messing, *Gene* 19:259–268, 1982), pCQV2 (Queen, ibid.), pMAL-2 (New England Biolabs, Beverly, Mass.) and derivatives thereof Plasmids may contain both viral and bacterial elements.

Given the teachings provided herein, promoters, terminators and methods for introducing expression vectors encoding IL-1 Type 3 receptors of the present invention into plant, avian and insect cells would be evident to those of skill in the art. The use of baculoviruses, for example, as vectors for expressing heterologous DNA sequences in insect cells has been reviewed by Atkinson et al. (*Pestic. Sci.* 28:215–224, 1990). In addition, the use of *Agrobacterium rhizogenes* as vectors for expressing genes in plant cells has been reviewed by Sinkar et al. (*J. Biosci.* (Bangalore) 11:47–58, 1987).

Host cells containing DNA molecules of the present invention are then cultured to express a DNA molecule encoding a IL-1 Type 3 receptor. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA molecules by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the IL-1 Type 3 receptors of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M. Cultured mammalian cells are generally cultured in commercially available serum-containing or serum-free media. Selection of a medium and growth conditions appropriate for the particular cell line used is within the level of ordinary skill in the art.

IL-1 Type 3 receptors may also be expressed in non-human transgenic animals, particularly transgenic warm-blooded animals. Methods for producing transgenic animals, including mice, rats, rabbits, sheep and pigs, are known in the art and are disclosed, for example, by Hammer et al. (*Nature* 315:680–683, 1985), Palmiter et al. (*Science* 222:809–814, 1983), Brinster et al. (*Proc. Natl. Acad. Sci. USA* 82:4438–4442, 1985), Palmiter and Brinster (Cell 41:343–345, 1985) and U.S. Pat. No. 4,736,866, which are incorporated herein by reference. Briefly, an expression unit, including a DNA sequence to be expressed together with appropriately positioned expression control sequences, is introduced into pronuclei of fertilized eggs. Introduction of DNA is commonly done by microinjection. Integration of the injected DNA is detected by blot analysis of DNA from tissue samples, typically samples of tail tissue. It is generally preferred that the introduced DNA be incorporated into the germ line of the animal so that it is passed on to the animal's progeny.

Within particularly preferred embodiments of the invention, "knockout" animals may be developed from embryonic stem cells through the use of homologous recombination (Capecchi, *Science* 244:1288–1292, 1989) or antisense oligonucleotide (Stein and Chen, *Science* 261(5124):1004–1012, 1993; Milligan et al., *Semin. Conc. Biol.* 3(6):391–398, 1992).

Within a preferred embodiment of the invention, a transgenic animal, such as a mouse, is developed by targeting a mutation to disrupt a IL-1 Type 3 receptor sequence (see Mansour et al., "Disruption of the proto-oncogene int-2 in mouse embryo-derived stem cells: A general strategy for targeting mutations to non-selectable genes," *Nature* 336:348–352, 1988). Such animals may readily be utilized as a model to study the role of the IL-1 Type 3 receptor in metabolism.

Soluble IL-1 Type 3 Receptors and Receptor Peptides

As noted above, the present invention also provides soluble IL-1 Type 3 receptors and receptor peptides. Within the context of the present invention, IL-1 Type 3 receptor peptides should be understood to include portions of a IL-1 Type 3 receptor or derivatives thereof discussed above, which do not contain transmembrane domains, and which are at least 8, and more preferably 10 or greater amino acids in length. Briefly, the structure of the IL-1 Type 3 receptor as well as putative transmembrane domains may be predicted from the primary translation products using the hydrophopicity plot function of, for example, PROTEAN (DNA STAR, Madison, Wis.), or according to the methods described by Kyte and Doolittle (*J. Mol. Biol.* 157:105–132, 1982). While not wishing to be bound by a graphical representation, based upon this hydrophopicity analysis, IL-1 Type 3 receptors are believed to have the general structure shown in FIG. 1. In particular, these receptors are believed to comprise an extracellular amino-terminal domain, a transmembrane domain, and an intracellular domain.

Within one aspect of the invention, isolated IL-1 Type 3 receptor peptides are provided comprising the extracellular amino-terminal domain of a IL-1 Type 3 receptor. Within a preferred embodiment, an isolated IL-1 Type 3 receptor peptide is provided comprising the sequence of amino acids shown in Sequence I.D. No.2, from amino acid number 1 to amino acid number 336. Within other embodiments, isolated IL-1 Type 3 receptor peptides are provided comprising the sequence of amino acids shown in Sequence I.D. No. 4, from amino acid number 1 to amino acid number 338.

IL-1 Type 3 receptor peptides may be prepared by, among other methods, culturing suitable host/vector systems to produce the recombinant translation products of the present invention. Supernatants from such cell lines may then be treated by a variety of purification procedures in order to isolate the IL-1 Type 3 receptor peptide. For example, the supernatant may be first concentrated using commercially available protein concentration filters, such as an Amicon or Mllipore Pellicon ultrafiltration unit. Following concentration, the concentrate may be applied to a suitable purification matrix such as, for example, IL-1 or an anti-IL-1 Type 3 receptor antibody bound to a suitable support. Alternatively, anion or cation exchange resins may be employed in order to purify the receptor or peptide. Finally, one or more reversed-phase high performance liquid chromatography (RP-HPLC) steps may be employed to further purify the IL-1 Type 3 receptor peptide.

Alternatively, IL-1 Type 3 receptor peptides may also be prepared utilizing standard polypeptide synthesis protocols, and purified utilizing the above-described procedures.

A IL-1 Type 3 receptor peptide is deemed to be "isolated" or purified within the context of the present invention, if only a single band is detected subsequent to SDS-polyacrylamide gel analysis followed by staining with Coomassie Brilliant Blue.

Antibodies to IL-1 Type 3 Receptors

Within one aspect of the present invention, IL-1 Type 3 receptors, including derivatives thereof, as well as portions or fragments of these proteins such as the IL-1 Type 3 receptor peptides discussed above, may be utilized to prepare antibodies which specifically bind to IL-1 Type 3 receptors. Within the context of the present invention the term "antibodies" includes polyclonal antibodies, monoclonal antibodies, fragments thereof such as F(ab')$_2$ and Fab fragments, as well as recombinantly produced binding partners. These binding partners incorporate the variable regions from a gene which encodes a specifically binding monoclonal antibody. Antibodies are defined to be specifically binding if they bind to the IL-1 Type 3 receptor with a $K_A$ of greater than or equal to $10^7$ M$^{-1}$ and preferably greater than or equal to $10^8$M$^{-1}$, and bind to IL-1 Type I or Type II receptors with an affinity of less than $K_A$ $10^7$ M$^{-1}$, and preferably less than $10^5$M$^{-1}$ or $10^3$M$^{-1}$. The affinity of a monoclonal antibody or binding partner may be readily determined by one of ordinary skill in the art (see Scatchard, *Ann. N.Y. Acad Sci.* 51:660–672, 1949).

Polyclonal antibodies may be readily generated by one of ordinary skill in the art from a variety of warm-blooded animals such as horses, cows, goats, sheep, dogs, chickens, rabbits, mice, or rats. Briefly, the IL-1 Type 3 receptor is utilized to immunize the animal through intraperitoneal, intramuscular, intraocular, or subcutaneous injections. The immunogenicity of a IL-1 Type 3 receptor or IL-1 Type 3 receptor peptide may be increased through the use of an adjuvant such as Freund's complete or incomplete adjuvant. Following several booster immunizations, small samples of serum are collected and tested for reactivity to the IL-1 Type 3 receptor. A variety of assays may be utilized in order to detect antibodies which specifically bind to a IL-1 Type 3 receptor. Exemplary assays are described in detail in *Antibodies: A Laboratory Manual*, Harlow and Lane (eds.), Cold Spring Harbor Laboratory Press, 1988. Representative examples of such assays include: Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos. 4,376,110 and 4,486,530; see also *Antibodies: A Laboratory Manual*, supra). Particularly preferred polyclonal antisera will give a signal that is at least three times greater than background. Once the titer of the animal has reached a plateau in terms of its reactivity to the IL-1 Type 3 receptor, larger quantities of polyclonal antisera may be readily obtained either by weekly bleedings, or by exsanguinating the animal.

Monoclonal antibodies may also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, within one embodiment a subject animal such as a rat or mouse is injected with a form of IL-1 Type 3 receptor suitable for generating an immune response against the IL-1 Type 3 receptor. Representative examples of suitable forms include, among others, cells which express the IL-1 Type 3 receptor, or peptides which are based upon the IL-1 Type 3 receptor sequence. Additionally, many techniques are known in the art for increasing the resultant immune response, for example, by coupling the receptor or receptor peptides to another protein such as ovalbumin or keyhole limpet hemocyanin (KLH), or through the use of adjuvants such as Freund's complete or incomplete adjuvant. The initial immunization may be through intraperitoneal, intramuscular, intraocular, or subcutaneous routes.

Between one and three weeks after the initial immunization the animal may be reimmunized with another booster immunization. The animal may then be test bled and the serum tested for binding to the IL-1 Type 3 receptor using assays as described above. Additional immunizations may also be accomplished until the animal has plateaued in its reactivity to the IL-1 Type 3 receptor. The animal may then be given a final boost of IL-1 Type 3 receptor or IL-1 Type 3 receptor peptide, and three to four days later sacrificed. At this time, the spleen and lymph nodes may be harvested and disrupted into a single cell suspension by passing the organs through a mesh screen or by rupturing the spleen or lymph node membranes which encapsidate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the IL-1 Type 3 receptor that is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein-Barr virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas*, 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63—Ag 8.653 (ATCC No. CRL 1580), which may be utilized for fusions with either mouse, rat, or human cell lines. Fusion between the myeloma cell line and the cells from the immunized animal may be accomplished by a variety of methods, including the use of polyethylene glycol (PEG) (see *Antibodies: A Laboratory Manual*, Harlow and Lane (eds.), Cold Spring Harbor Laboratory Press, 1988) or electrofusion (see Zimmerman and Vienken, *J. Membrane Biol.* 67:165–182, 1982).

Following the fusion, the cells are placed into culture plates containing a suitable medium, such as RPMI 1640 or DMEM (Dulbecco's Modified Eagles Medium) (JRH Biosciences, Lenexa, Kans.). The medium may also contain additional ingredients, such as Fetal Bovine Serum ("FBS," i.e., from Hyclone, Logan, Utah, or JRH Biosciences), thymocytes which were harvested from a baby animal of the same species as was used for immunization, or agar to solidify the medium. Additionally, the medium should contain a reagent which selectively allows for the growth of fused spleen and myeloma cells. Particularly preferred is the use of HAT (hypoxanthine, aminopterin, and thymidine) (Sigma Chemical Co., St. Louis, Mo.). After about seven days, the resulting fused cells or hybridomas may be screened in order to determine the presence of antibodies which recognize the IL-1 Type 3 receptor. Following several clonal dilutions and reassays, a hybridoma producing antibodies which bind to IL-1 Type 3 receptor may be isolated.

Other techniques may also be utilized to construct monoclonal antibodies (see Huse et al., "Generation of a Large Combinational Library of the Immunoglobulin Repertoire in Phage Lambda," *Science* 246:1275–1281, December 1989; see also Sastry et al., "Cloning of the Immunological Repertoire in *Escherichia coil* for Generation of Monoclonal Catalytic Antibodies: Construction of a Heavy Chain Variable Region-Specific cDNA Library," *Proc. Natl. Acad. Sci. USA* 86:5728–5732, August 1989; see also Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population and utilized to create heavy and light chain immunoglobulin cDNA expression libraries in the kIMMUNOZAP(H) and kIMMUNOZAP(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. The construction of these proteins may be readily accomplished by one of ordinary skill in the art (see Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989; see also, U.S. Pat. No. 5,132,405 entitled "Biosynthetic Antibody Binding Sites"), given the disclosure provided herein. Briefly, within one embodiment, DNA molecules encoding IL-1 Type 3 receptor-specific antigen binding domains are amplified from hybridomas which produce a specifically binding monoclonal antibody, and inserted directly into the genome of a cell which produces human antibodies (see Verhoeyen et al., Supra; see also Reichmann et al., supra). This technique allows the antigen-binding site of a specifically binding mouse or rat monoclonal antibody to be transferred into a human antibody. Such antibodies are preferable for therapeutic use in humans because they are not as antigenic as rat or mouse antibodies.

Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or IL-1 Type 3 receptor binding domain of the antibody may be found in the variable region of the antibody. Furthermore, DNA sequences which encode smaller portions of the antibody or variable regions which specifically bind to mammalian IL-1 Type 3 receptor may also be utilized within the context of the present invention. These portions may be readily tested for binding specificity to the IL-1 Type 3 receptor utilizing assays described below.

Within a preferred embodiment, genes which encode the variable region from a hybridoma producing a monoclonal antibody of interest are amplified using oligonucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{Hl}$, $V_L$ and $C_L$ regions. These primers may be utilized to amplify heavy or light chain variable regions, which may then be inserted into vectors such as IMMUNOZAP*(H) or IMMUNOZAP*(L) (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426, 1988).

Other "antibodies" which may also be prepared utilizing the disclosure provided herein, and thus which are also deemed to fall within the scope of the present invention include humanized antibodies (e.g., U.S. Pat. No. 4,816,567 and WO 94/10332), micobodies (e.g., WO 94/09817) and transgenic antibodies (e.g., GB 2 272 440).

Once suitable antibodies have been obtained, they may be isolated or purified by many techniques well known to those of ordinary skill in the art (see *Antibodies: A Laboratory Manual*, supra). Suitable techniques include peptide or protein affinity columns, HPLC or RP-HPLC, purification on protein A or protein G columns, or any combination of these techniques. Within the context of the present invention, the term "isolated" as used to define antibodies or binding partners means "substantially free of other blood components."

Antibodies of the present invention have many uses. For example, antibodies may be utilized in flow cytometry to sort IL-1 Type 3 receptor-bearing cells, or to histochemically stain IL-1 Type 3 receptor-bearing tissues. Briefly, in order to detect IL-1 Type 3 receptors on cells, the cells (or tissue) are incubated with a labeled antibody which specifically binds to IL-1 Type 3 receptors, followed by detection of the presence of bound antibody. These steps may also be accomplished with additional steps such as washings to remove unbound antibody. Representative examples of suitable labels, as well as methods for conjugating or coupling antibodies to such labels are described in more detail below.

In addition, purified antibodies may also be utilized therapeutically to block the binding of IL-1 or other IL-1 Type 3 receptor substrates to the IL-1 Type 3 receptor in vitro or in vivo. As noted above, a variety of assays may be utilized to detect antibodies which block or inhibit the binding of IL-1 to the IL-1 Type 3 receptor, including inter alia, inhibition and competition assays noted above. Within one embodiment, monoclonal antibodies (prepared as described above) are assayed for binding to the IL-1 Type 3 receptor in the absence of IL-1, as well as in the presence of varying concentrations of IL-1. Blocking antibodies are identified as those which, for example, bind to IL-1 Type 3 receptors and, in the presence of IL-1, block or inhibit the binding of IL-1 to the IL-1 Type 3 receptor.

Antibodies of the present invention may also be coupled or conjugated to a variety of other compounds (or labels) for either diagnostic or therapeutic use. Such compounds include, for example, toxic molecules, molecules which are nontoxic but which become toxic upon exposure to a second compound, and radionuclides. Representative examples of such molecules are described in more detail below.

Antibodies which are to be utilized therapeutically are preferably provided in a therapeutic composition comprising the antibody or binding partner and a physiologically acceptable carrier or diluent. Suitable carriers or diluents include, among others, neutral buffered saline or saline, and may also include additional excipients or stabilizers such as buffers, sugars such as glucose, sucrose, or dextrose, chelating agents such as EDTA, and various preservatives.

Labels

The nucleic acid molecules, antibodies, and IL-1 Type 3 receptors (including sIL-1 3R) of the present invention may be labeled or conjugated (either through covalent or non-covalent means) to a variety of labels or other molecules, including for example, fluorescent markers, enzyme markers, toxic molecules, molecules which are nontoxic but which become toxic upon exposure to a second compound, and radionuclides.

Representative examples of fluorescent labels suitable for use within the present invention include, for example, Fluorescein Isothiocyanate (FITC), Rhodamine, Texas Red, Luciferase and Phycoerythrin (PE). Particularly preferred for use in flow cytometry is FITC which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; and Goding, "Conjugation of Antibodies with Fluorochromes: Modification to the Standard Methods," *J. Immunol. Methods* 13:215–226, 1970.) For histochemical staining, HRP, which is preferred, may be conjugated to the purified antibody according to the method of Nakane and Kawaoi ("Peroxidase-Labeled Antibody: A New Method of Conjugation," *J. Histochem. Cytochem.* 22:1084–1091, 1974; see also, Tijssen and Kurstak, "Highly Efficient and Simple Methods for Preparation of Peroxidase and Active Peroxidase Antibody Conjugates for Enzyme Immunoassays," *Anal. Biochem.* 136:451–457, 1984).

Representative examples of enzyme markers or labels include alkaline phosphatase, horse radish peroxidase, and β-galactosidase. Representative examples of toxic molecules include ricin, abrin, diphtheria toxin, cholera toxin, gelonin, pokeweed antiviral protein, tritin, Shigella toxin, and Pseudomonas exotoxin A. Representative examples of molecules which are nontoxic, but which become toxic upon exposure to a second compound include thymidine kinases such as HSVTK and VZVTK. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212.

As will be evident to one of skill in the art given the disclosure provided herein, the above described nucleic acid molecules, antibodies, and IL-1 Type 3 receptors may also be labeled with other molecules such as colloidal gold, as well either member of a high affinity binding pair (e.g., avidin-biotin).

Diagnostic use of IL-1 Type 3 Receptor Sequences

Within another aspect of the present invention, probes and primers are provided for detecting IL-1 Type 3 receptors. Within one embodiment of the invention, probes are provided which are capable of hybridizing to IL-1 Type 3 receptor DNA or RNA. For purposes of the present invention, probes are "capable of hybridizing" to IL-1 Type 3 receptor DNA if they hybridize to Sequence I.D. Nos. 1 or 3 under conditions of moderate or high stringency (see Sambrook et al., supra); but not to IL-1 Type I or Type II receptor nucleic acid sequences. Preferably, the probe may be utilized to hybridize to suitable nucleotide sequences in the presence of 50% formamide, 5×SSPE, 5×Denhardt's, 0.1% SDS and 100 ug/ml Salmon Sperm DNA at 42° C., followed by a first wash with 2×SSC at 42° C., and a second wash with 0.2×SSC at 55 to 60° C.

Probes of the present invention may be composed of either deoxyribonucleic acids (DNA) ribonucleic acids (RNA), nucleic acid analogues, or any combination of these, and may be as few as about 12 nucleotides in length, usually about 14 to 18 nucleotides in length, and possibly as large as the entire sequence of the IL-1 Type 3 receptor. Selection of probe size is somewhat dependent upon the use of the probe. For example, in order to determine the presence of various polymorphic forms of the IL-1 Type 3 receptor within an individual, a probe comprising virtually the entire length of the IL-1 Type 3 receptor coding sequence is preferred. IL-1 Type 3 receptor probes may be utilized to identify polymorphisms linked to the IL-1 Type 3 receptor gene (see, for example, Weber, *Genomics* 7:524–530, 1990; and Weber and May, *Amer. J. Hum. Gen.* 44:388–396, 1989). Such polymorphisms may be associated with inherited diseases such as diabetes.

Probes may be constructed and labeled using techniques which are well known in the art. Shorter probes of, for example, 12 or 14 bases may be generated synthetically. Longer probes of about 75 bases to less than 1.5 kb are preferably generated by, for example, PCR amplification in the presence of labeled precursors such as $^{32}$P-dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells (see Sambrook et al., supra).

Probes may be labeled by a variety of markers, including, for example, radioactive markers, fluorescent markers, enzymatic markers, and chromogenic markers. The use of $^{32}$P is particularly preferred for marking or labeling a particular probe.

Probes of the present invention may also be utilized to detect the presence of a IL-1 Type 3 receptor mRNA or DNA within a sample. However, if IL-1 Type 3 receptors are present in only a limited number, or if it is desired to detect a selected mutant sequence which is present in only a limited number, or if it is desired to clone a IL-1 Type 3 receptor from a selected warm-blooded animal, then it may be beneficial to amplify the relevant sequence such that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), an d DNA amplification utilizing Polymerase Chain Reaction ("PCR") (see U.S. Pat. Nos. 4,683,195, 4,683,202, and 4,800,159) (see also, U.S. Pat. Nos. 4,876, 187, and 5,011,769, which describe an alternative detection/ amplification system comprising the use of scissile linkages).

Within a particularly preferred embodiment, PCR amplification is utilized to detect or obtain a IL-1 Type 3 receptor DNA. Briefly, a s described in reater detail below, a DNA sample is denatured at 95° C. in order to generate single stranded DNA. Specific primers, as discussed below, are then annealed at 37° C. to 70° C., depending on the proportion of AT/GC in the primers. The primers are extended at 72° C. with Taq polymerase in order to generate the opposite strand to the template. These steps constitute one cycle, which may be repeated in order to amplify the selected sequence.

Primers for the amplification of a selected sequence should be selected from sequences which are highly specific and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and may be easily synthesized using techniques well known in the art.

Pharmaceutical Compositions and Therapeutic Uses

As noted above, the present invention provides pharmaceutical compositions, as well as methods for using the same (for either prophylactic or therapeutic use). Briefly, the pharmaceutical compositions of the present invention may comprise an IL-1 3R, sIL-1 3R, antibody which is capable of specifically binding IL-1 3R, IL-1 3R antagonists or agonists, in combination with a pharmaceutically acceptable carrier, diluent, or excipient. Such compositions may comprise buffers such as neutral buffered saline, phosphate buffered saline and the like, carbohydrates such as glucose, mannose, sucrose or dextrose, proteins, polypeptides or amino acids, antioxidants, chelating agents such as EDTA or glutathione, and preservatives.

Compositions of the present invention may be formulated for the manner of administration indicated, including for example, for oral, nasal, venous, vaginal or rectal administration. Within other embodiments, the compositions may be administered as part of a sustained release implant (e.g., intra-articularly). Within yet other embodiments, the compositions may be formulized as a lyophilizate, utilizing appropriate excipients which provide stability as a lyophilizate, and subsequent to rehydration.

Pharmaceutical compositions of the present invention may be utilized in order to treat a wide variety of diseases including, for example, immune-associated diseases such as rheumatoid arthritis, inflammatory bowel disease, multiple sclerosis, myasthemia gravis, scleritis, scleroderma, septic shock, allograft rejection, and graft versus host (GVH) disease. In particular, pharmaceutical compositions of the present invention may be administered in a manner appropriate to the disease to be treated (or prevented). Although appropriate dosages may be determined by clinical trials, the quantity and frequency of administration will be determined by such factors as the condition of the patient, and the type and severity of the patient's disease.

Within other aspects of the present invention, viral vectors are provided which may be utilized to treat diseases wherein either the IL-1 Type 3 receptor (or a mutant IL-1 Type 3 receptor) is over-expressed, or where no IL-1 Type 3 receptor is expressed. Briefly, within one embodiment of the invention, viral vectors are provided which direct the production of antisense IL-1 Type 3 receptor RNA, in order to prohibit the over-expression of IL-1 Type 3 receptors, or the expression of mutant IL-1 Type 3 receptors. Within another embodiment, viral vectors are provided which direct the expression of IL-1 Type 3 receptor cDNA. Viral vectors suitable for use in the present invention include, among others, recombinant vaccinia vectors (U.S. Pat. Nos. 4,603, 112 and 4,769,330), recombinant pox virus vectors (PCT Publication No. WO 89/01973), and preferably, recombinant retroviral vectors ("Recombinant Retroviruses with Amphotropic and Ecoptropic Host Ranges," PCT Publication No. WO 90/02806; "Retroviral Packaging Cell Lines and Processes of Using Same," PCT Publication No. WO 89/07150; and "Antisense RNA for Treatment of Retroviral Disease States," PCT Publication No. WO/03451), and herpesvirus vectors (Kit, Adv. Exp. Med. Biol. 215:219–236, 1989; U.S. Pat. No. 5,288,641).

Within various embodiments of the invention, the above-described compositions may be administered in vivo, or ex vivo. Representative routes for in vivo administration include intradermally ("i.d."), intracranially ("i.c."), intraperitoneally ("i.p."), intrathecally ("i.t."), intravenously ("i.v."), subcutaneously ("s.c.") or intramuscularly ("i.m.").

Within other embodiments of the invention, the vectors which contain or express nucleic acid molecules of the present invention, or even the nucleic acid molecules themselves, may be administered by a variety of alternative techniques, including for example direct DNA injection (Acsadi et al., Nature 352:815–818, 1991); microprojectile bombardment (Williams et al., PNAS 88:2726–2730, 1991); liposomes (Pickering et al., Circ. 89(1):13–21, 1994; and Wang et al., PNAS 84:7851–7855, 1987); lipofection (Felgner et al., Proc. Natl. Acad. Sci. USA 84:7413–7417, 1989); DNA ligand (Wu et al., J. of Biol. Chem. 264:16985–16987, 1989); administration of DNA linked to killed adenovirus (Michael et al., J. Biol. Chem. 268(10):6866–6869, 1993; and Curiel et al., Hum. Gene Ther. 3(2):147–154, 1992), retrotransposons, cytofectin-mediated introduction (DMRIE-DOPE, Vical, Calif.) and transferrin-DNA complexes (Zenke).

The following examples are offered by way of illustration, and not by way of limitation.

EXAMPLES

Example 1

Isolation of Interleukin-1 Type 3 Redeptor cDNA

A. Isolation of Interleukin-1 Type 3 Receptor cDNA From a Rat Lung cDNA Library

Male Sprague-Dawley rats (Madison, Wis.) weighing between 175–250 gm are decapitated, and the lungs excised. Total RNA is then isolated from the lung utilizing a Promega RNAgents Total RNA Kit (catalog #Z5110, Promega, Wis.) according to the manufacturers instructions, followed by the isolation of poly A+RNA utilizing a Promega PolyATract kit (catalog #Z5420). A cDNA phage library is then prepared utilizing a Giga-Pack Gold library construction kit according to the manufacturers' instructions (catalog #237611, Stratagene, LaJolla, Calif.), which is in turn plated and screened essentially as described by Sambrook et al., (Molecular Cloning) with oligonucleotide (5'-CTTCAACTGC ACATACCCTC CAGTAACAAA CGGGGCAGTG AATCTGACAT-3') (Sequence I.D. No. 6). This oligonucleotide is complementary to nucleotides 211–260 of the rat IL-1 Type 3 receptor cDNA sequence shown in Sequence I.D. No. 3.

The phage library is rescreened until a single pure phage isolate is obtained. The phage is then grown on bacterial host XL1-Blue (Stratagene, LaJolla, Calif.), and plasmid DNA is excised with ExAssist helper phage (Stratagene) in SOLR cells. The SOLR cells are then plated, and plasmid DNA is isolated and sequenced utilizing the Sanger dideoxy protocol.

A rat IL-1 Type 3 receptor cDNA sequence that may be obtained utilizing this procedure is set forth in Sequence I.D. No. 3.

B. Isolation of Interleukin-1 Type 3 Receptor cDNA From a Commerically Available Rat cDNA Library IL-1 Type 3 receptor cDNA can also be isolated from commercially available rat cDNA libraries. For example, two million plaques from a rat phage library (Clontech, catalog #RL1048a) may be plated according to the manufacturer's instructions, and screened with oligonucleotide Sequence I.D. No. 6 essentially as described above.

A rat IL-1 Type 3 receptor cDNA sequence that may be obtained utilizing this procedure is set forth in Sequence I.D. No.3.

C. Isolation of IL-1 Type 3 Receptor cDNA From a Human cDNA Library

IL-1 Type 3 receptor cDNA can also be isolated from commercially available human cDNA libraries. Briefly, approximately two million plaques from a human phage library (Clontech, catalog #HL1158a) are plated according to the manufacturers instructions, and screened with oligonucleotide (5'-CCTCCCATAA CATCTGGGGA AGT-CAGTGTA ACATGGTATA AAAATTCTAG C-3') (Sequence I.D. No. 7) essentially as described above. This oligonucleotide is complementary to nucleotides 260–310 of the human IL-1 Type 3 receptor cDNA sequence shown in Sequence I.D. No. 1.

The phage library is rescreened and isolated as described above. The human sequence that is obtained utilizing this procedure is approximately 89.1% identical at the nucleotide level and 89.2% identical at the amino acid level to that of the common region of the above-described rat IL-1 Type 3 receptors.

Example 2

Expression of IL-1 Type 3 Receptor cDNA

A. Expression of Rat Interleukin-1 Type 3 Receptor

In order to express IL-1 Type 3 receptor cDNA, a mammalian cell expression vector (pCDM7amp) is first constructed. Briefly, pCDM7amp is a DNA plasmid which contains 1) an ampicillin resistance gene that provides for selection in prokaryotic cells, 2) a bacterial origin of replication which allows propagation and amplification in host bacterial cells, 3) a CMV (cytomegalovirus) promoter which sponsors transcription in mammalian cells, 4) a multiple cloning site (MCS), which is a series of adjacent restriction sites in the DNA sequence that are useful for the insertion of appropriate DNA fragments, and 5) a SV 40 T-antigen splice and polyadenylation site.

pCDM7-Amp is constructed from pCDM8 (Seed, Nature 329:840–842, 1987; Seed and Aruffo, Proc. Natl. Acad. Sci. 84:3365–3369, 1987; Thomsen et al., Cell 63:485–493, 1990; Bernot and Auffray, Proc. Natl. Acad. Sci 88:2550–2554, 1991; Han et al., Nature 349:697–700, 1991) by deletion of the adeno origin of replication, M13 origin of replication and sup F selection marker. An ampicillin resistance marker is then added in order to facilitate selection of the plasmid.

A full-length rat IL-1 Type 3 receptor clone in pBluescriptSK—is isolated from the phage clone described above, and cut with EcoRV and HindIII, releasing two inserts. The inserts are then isolated and ligated to pCDM7-Amp which had been similarly cut. The resulting product is used to transform E. coli DH5α, and colonies are examined by restriction digests for correct orientation of the two inserts (i.e., proper formation of the IL-1 Type 3R coding sequence.)

COS-7 (ATCC No. CRL 1651) cells are then transfected with pCDM7-Amp containing IL-1 Type 3 receptor cDNA (10 ug DNA/10 cm plate of cells) utilizing 400 μg/ml of DEAE-Dextran and 100 μM chloroquine. The cells are transfected for 4 hours, then shocked with 10% DMSO for 2 minutes. The cells are then washed, and grown in DMEM containing 10% Fetal Bovine Serum for 2 days in a 24-well plate.

B. Expression of Human Interleukin-1 Type 3 Receptor

A full-length human IL-1 Type 3 receptor clone in pBluescriptSK—is isolated from the phage clone described above, and cut with NotI and XhoI, releasing the insert. The insert is then isolated and ligated to pCDM7-Amp which had been similarly cut. The resulting product is used to transform E. coli DH5α, from which larger quantities of plasmid DNA may be isolated.

COS-7 (ATCC No. CRL 1651) cells are then transfected with pCDM7-Amp containing IL-1 Type 3 receptor cDNA (10 ug DNA/10 cm plate of cells) utilizing 400 μg/ml of DEAE-Dextran and 100 μM chloroquine. The cells are transfected for 4 hours, then shocked with 10% DMSO for 2 minutes. The cells are then washed, and grown in DMEM containing 10% Fetal Bovine Serum for 2 days in a 24-well plate.

Example 3

Construction and Expression of Soluble Human Interleuklin-1 Type 3 Receptor

A. Plasmid Construction

1. Vector Preparation

An expression vector containing the N-terminal portion of the human IL-1 type 3 receptor, also referred to as the "soluble" form of the receptor, is constructed essentially as described below. Briefly, pCDM7amp DNA (as described above) is subjected to restriction endonuclease digestion with two enzymes, NotI and XhoI, each of which have one recognition site in this vector, both located in the MCS. The product is a linearized DNA fragment with the CMV promoter/enhancer immediately upstream of the cut site, and the polyadenylation signal downstream of the cut site.

After digestion, the cleaved vector is isolated by agarose gel electrophoresis and purified using the Gene Clean procedure (Bio 101, San Diego, Calif.). The vector is now ready to combine with a DNA fragment encoding the soluble human IL-1 type 3 receptors.

2. Insert Preparation

Into this prepared vector is ligated a DNA fragment containing the coding region of the first 336 amino acids of the human IL-1 type 3 receptor set forth in Sequence ID No. 1 (from nucleotide number 129 to nucleotide number 1136).

Briefly, two oligonucleotides are first synthesized for use as primers in PCR. These oligonucleotides can be synthesized on a DNA synthesizer. The first primer consists of the sequence 5'-CCTACTCGAG ATGTGGTCCT TGCTGCTC-3'(Sequence ID No: 8). The first four nucleotides of this sequence serve as a spacer, and increase the efficiency of endonuclease cleavage in a subsequent reaction to be described. Nucleotides 5 through 10 encode a XhoI endonuclease cleavage site, and nucleotides 11 through 28 are identical to the N-terminal coding region of the human IL-type 3 receptor (nucleotides 129 to 146 in Sequence ID No: 1)).

The second primer consists of the sequence 5'-ATGCGCGGCC GCCTATCGAA AATCCGGAGC TGG-3' (Sequence Id No: 9). The first four nucleotides of this sequence serve as a spacer, and increase efficiency of endonuclease cleavage in a subsequent reaction to be described. Nucleotides 5 through 12 encode a NotI endonuclease cleavage site. Nucleotides 13 through 15 encode a translation stop codon, and nucleotides 16 though 33 are complementary to the coding region of the human IL-1 type 3 receptor immediately preceding the transmembrane region (nucleotides 1133 through 1116 in Sequence ID No. 1).

The fragment encoding soluble human IL-1 type 3 receptor is then generated by PCR. Briefly, 100 ng of each primer are combined in a 0.5 ml test tube, along with 1 ng of the entire human IL-1 type 3 receptor DNA sequence contained in a cloning vector, such as Bluescript (Stratagene, La Jolla, Calif.). Ten microliters of 10×PCR buffer, 5 ul of 25 mM MgCl, 1 ul of 25 mM aTP, and 1 ul of Taq polymerase/Vent polymerase (16:1 ratio) are also added to the reaction. The complete sample is then overlayed with 100 ul of mineral oil to prevent evaporation, and the sample is placed in a thermocycler. Reaction conditions are: 94° C. for 15 seconds, 55° C. for 60 seconds, and 72° C. for 60 seconds. These conditions are repeated for 25 cycles.

Product from the reaction is analyzed by agarose gel electrophoresis to verify the size of the fragment (1009 bp) and also to determine the approximate amount of DNA generated. The DNA is then isolated by phenol/chloroform extraction and purified over a G-50 mini-spin column (Boehringer Mannheim, Indianapolis, Ind.). Approximately 10 ug of the purified DNA fragment is digested with 20 units each of XhoI and NotI restriction endonucleases in a standard reaction to generate cohesive ends on the fragment which are compatible with the pCDM7 vector prepared as detailed above. The digested fragment is then agarose gel purified to remove impurities and contaminating DNA species.

3. Ligation

One hundred nanograms of vector DNA is combined with 100 ng of insert DNA in a 1.5 ml mini-tube with 1 ul of 10×ligation buffer, 1 ul of DNA ligase (Boehringer Mannheim), and water to a total volume of 10 ul. This sample is incubated at 23° C. for 2 hours.

4. Transformation

One hundred microliters of competent E. coli bacteria cells are combined with the ligation product and incubated on ice for 30 minutes. The sample is then incubated at 42° C. for 45 seconds. One milliliter of bacterial medium (Circle Grow, Bio 101, San Diego, Calif.) is then added, and the sample is shaken at 37° C. for 60 minutes. The sample is then plated on a bacterial growth plate containing bacterial medium and ampicillin at 100 ug/ml (Fisher Scientific), and incubated for 16 hours at 37° C.

5. Construct verification

Ten colonies from the ampicillin plate are selected and grown in 1 ml of bacterial medium for 24 hours. One hundred microliters of each culture is stored by adding an equal volume of 50% glycerol solution and frozen at −70° C. in mini-tubes. Plasmid DNA is then extracted from the remaining cultures by the mini-prep procedure essentially as described by Maniatis et al. (supra), and the recovered DNAs are analyzed by restriction digest with XhoI and NotI restriction endonucleases. The products of restriction digest are visualized by agarose gel electrophoresis and ethidium bromide staining. Correct plasmids will yield two bands: a vector band of approximately 3 kilobases, and an insert fragment of 1009 bases.

The frozen stock of a colony containing the correct plasmid is used to inoculate one liter of bacterial growth medium containing ampicillin (100 ug/ml). The culture is shaken at 37° C. for 24 hours, and plasmid DNA is isolated by a maxi-prep procedure (Promega). The portion on this plasmid coding for soluble human IL-1 type 3 receptor is analyzed by DNA sequencing (U.S. Biochemical) in order to verify that the sequence is correct.

B. Transfection Procedure and Expression

COS-7 (ATCC No. CRL 1651) or L-tk⁻ cells (ATCC No. CCL 1.3) are seeded at 1×10⁶ or 3×10⁶ cells on 10 cm tissue culture dishes and incubated over night. Cells are then transfected by a standard DEAE dextran method. Briefly, 10 μg of IL-1 type 3 receptor expression plasmid DNA are diluted in 3 ml of Dulbecco's modified Minimum Essential Medium (D-MEM) supplemented with glutamine, pyruvate, 25 mM HEPES, 100 microgram/ml DEAE dextran (0.5 Md., Sigma, St. Louis) and 0.1 mM chloroquine (Sigma). Cells are incubated in this transfection mixture for 4 hours at 37° C. After one washing step with D-MEM cells are incubated for 48 hours in D-MEM supplemented with 10% fetal calf serum. At this stage cells are ready for further analysis of the expressed IL-1 type 3 receptor.

Example 4

Signaling of IL-1 via the IL-1 Type 3 Receptor in a Functional Assay

IL-1 type 1 receptor cDNA and type 3 receptor cDNA are separately transfected into Jurkat cells (ATCC no. TIB 152) together with a reporter plasmid consisting of the HIV promoter region (HIV-LTR) linked to the bacterial chloramphenicol acetyltransferase (CAT) gene. Stimulation of the transfected cells with human IL-1 alpha leads through a signaling cascade involving the transcription factor NF-kappaB to the production of CAT, which in turn can be measured by commercially available assays (Promega, Madison, Wis.) (see also Leung et al., *J. Biol. Chem.* 269:1579–1582, 1994).

Figures 2, 3:
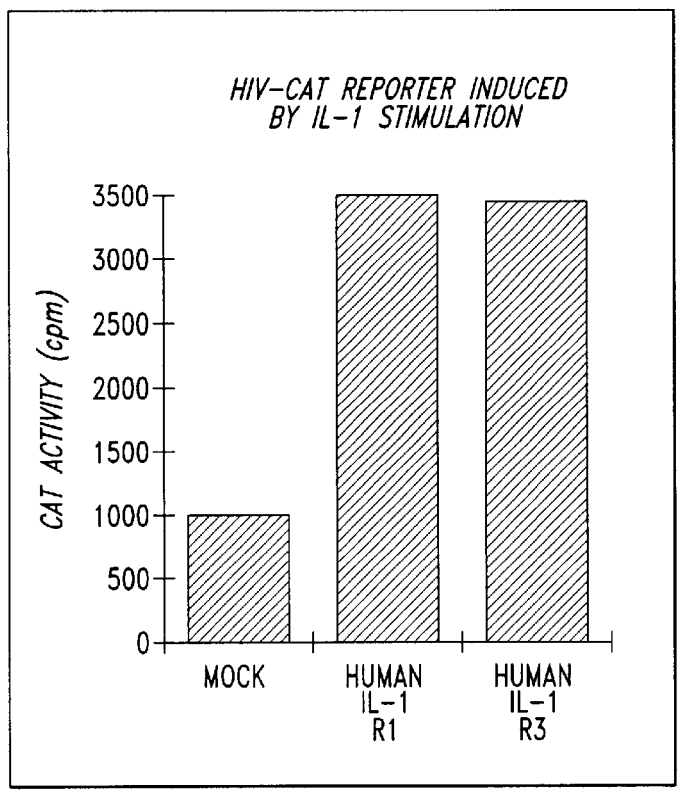
FIG. 2 is a table which lists the homology of a human IL-1 type 3 receptor with its rat homologue, and other interleukin receptors.
FIG. 3 is a graph which shows stimulation of a reporter product via a human IL-1 type 3 receptor.

Results are shown in FIG. 3. Briefly, approximately equal stimulation of CAT activity for both receptors can be seen over mock transfected control cells. This indicates that human IL-1 alpha can signal through the IL-1 type 3 receptor.

Example 5

Expression, Localization, and Activity of the IL-1 Type 3 Receptor

A. Expression Pattern of the IL-1 Type 3 Receptor

In order to determine in which rat tissues and parts of the rat brain the IL-1 Type 3 receptor is expressed, RNA protection assays are performed. Briefly, total RNA is isolated from each tissue or part of the brain and annealed at 65° C. to ³²P-labeled RNA generated from a plasmid containing a 600 bp fragment which covers the entire transmembrane region and portions of the extracellular and intracellular domains of the Type 3 receptor cDNA. Samples are then digested with RNase and fractionated on a denaturing polyacrylamice gel. The gel is then dried and the radioactivity quantitated using a Phospholmager (FIG. 4).

Figure 4:
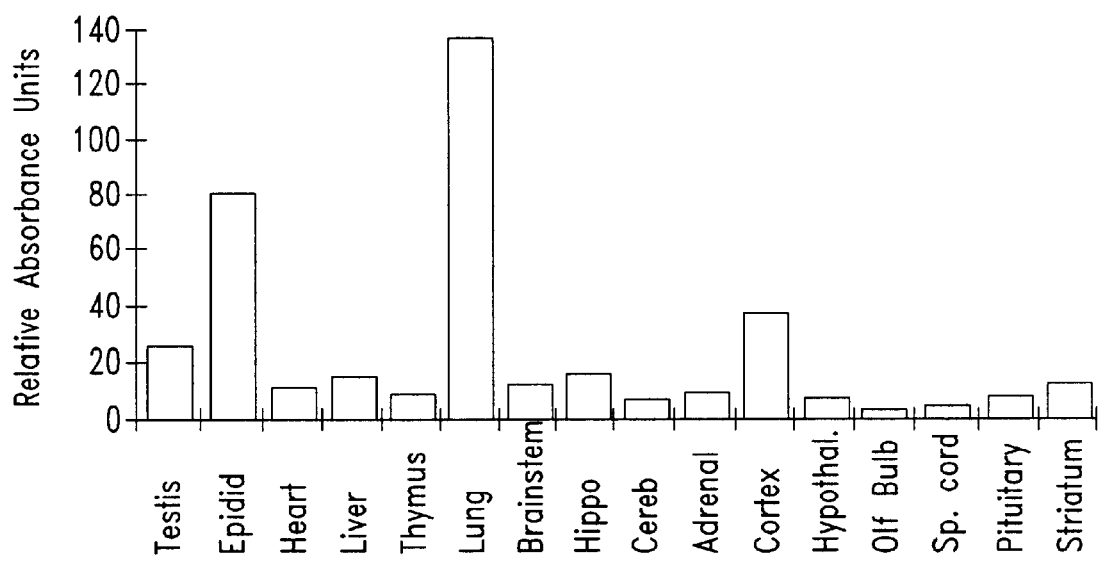
FIG. 4 is a graph which shows the expression pattern of the IL-1 Type 3 receptor based upon RNA protection assays.

As can be seen in FIG. 4, the highest level of expression is in the lung, followed by the epididymus and testis. When various areas of the brain are examined, the cerebral cortex contains the highest level of the Type 3 receptor, although other areas of the brain were also positive.

B. Localization of the IL-1 Type 3 Receptor by In Situ Hybridization

Utilizing in situ hybridization histochemistry, the IL-1 type 3 receptor may be found in the thymus and the spleen. In the thymus the signal is most prominent in the cortical region and not in the medulla. Within the rat brain the IL-1 type 3 receptor expression is detectable in the hippocampus and the fourth ventricle. This is in contrast to the localization of the IL-1 type 1 receptor which is restricted to the dentate gyrus granule cells.

Briefly, dissected tissue is frozen in isopentane cooled to −42° C. and subsequently stored at −80° C. prior to sectioning on a cryostat. Slide-mounted tissue sections are then stored at −80° C. Sections are removed from storage and placed directly into 4% buffered paraformaldehyde at room temperature. After 60 minutes, slides are rinsed in isotonic phosphate buffered saline (10 min.) and treated with proteinase K (1 μg/ml in 100 mM Tris/HCl, pH 8.0) for 10 minutes at 37° C. Subsequently, sections are successively washed in water (1 min.), 0.1 M triethanolamine (pH 8.0, plus 0.25% acetic anhydride) for 10 minutes and 2×SSC (0.3 mM NaCl, 0.03 mM sodium citrate, pH 7.2) for 5 minutes. Sections are then dehydrated through graded alcohols and air dried. Post-fixed sections are hybridized with 1.0×10⁶ dpm [35S]UTP-labeled riboprobes in hybridization buffer containing 75% formamide, 10% dextran sulphate, 3×SSC, 50 mM sodium phosphate buffer pH 7.4), 1×Denhardt's solution, 0.1 mg/ml yeast tRNA and 10 mM dithiothreitol in a total volume of 30 μl. The diluted probe is applied to sections on a glass coverslip and hybridized overnight at 55° C. in a humid environment. Post-hybridization, sections are washed in 2×SSC for 5 minutes and then treated with RNase A (200 μg/ml in 10 mM Tris/HCl, pH 8.0, containing 0.5 M NaCl) for 60 minutes at 37° C. Subsequently, sections are washed in 2×SSC for 5 minutes, 133 SSC for 5 minutes, 0.1×SSC for 60 minutes at 70° C., 0.5 ×SSC at room temperature for 5 minutes and then dehydrated in graded alcohols and air dried. For signal detection, sections are placed on Kodak Bio Max X-ray film and exposed for the required length of time or dipped in photographic emulsion (Amsersham LM-1) for high resolution analysis. Autoradiograms are analyzed using automated image analysis (DAGE camera/Mac II) while dipped sections were examined using a Zeiss Axioscope.

C. Inhibition of Thymocyte Proliferation by the IL-1 Type 3 Receptor

Ability of the IL-1 type 3 receptor to inhibit mouse thymocyte proliferation may also be examined. Briefly, the proliferative response of T lymphocyte lectins such as phytohemagglutin (PHA) is very low, but is markedly enhanced by IL-1. Thus, soluble type human and rat type 3 receptors may be utilized to competitively inhibit proliferation of mouse thymocytes stimulated by IL-1. Soluble human Type 1 receptor produced in baculovirus may be used as a positive control.

Briefly, soluble IL-1 type 1 or type 3 receptors are added to wells of a 96 well plate and serially diluted IL-1 is also added. Thymi are removed from young mice and a single cell suspension prepared in tissue culture media. Cells are washed 3 times and resuspended at a concentration of 10⁷ cells/ml. Cells are plated at 100 microliters in a 96 well flat bottom microtiter plate. PHA is added to stimulate the cells. Plates are then incubated for 48 hours in a 37° C., 5% CO₂ humidified incubator, and [³H] thymidine is added to the cells for the last 4 to 6 hours. Cells are then harvested and the [³H] thymidine incorporation determined by liquid scintillation counting.

Figure 5A:
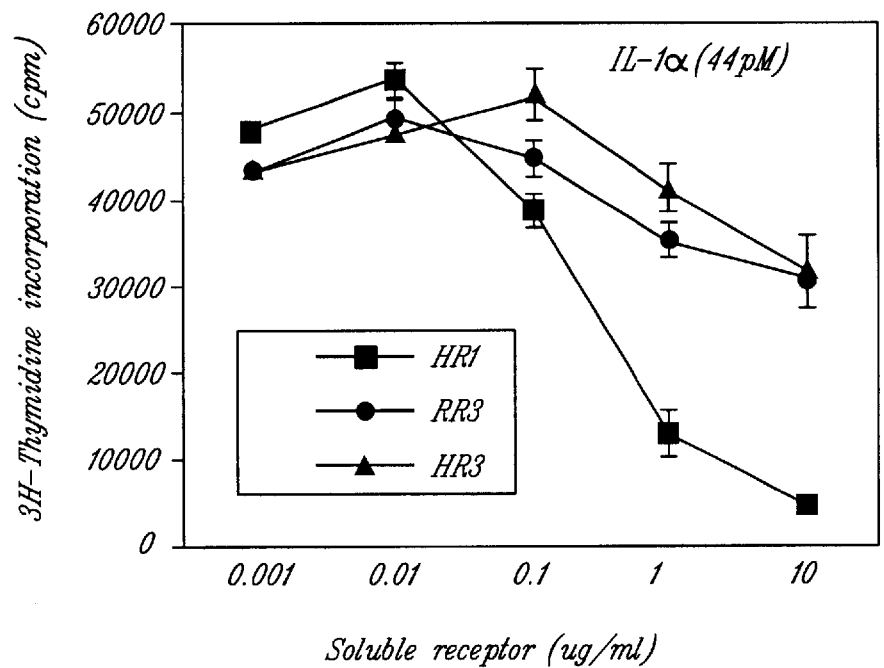
FIGS. 5A and B are two graphs which show inhibition of thymocyte proliferation by soluble IL-1 receptors.z
Figure 5B:
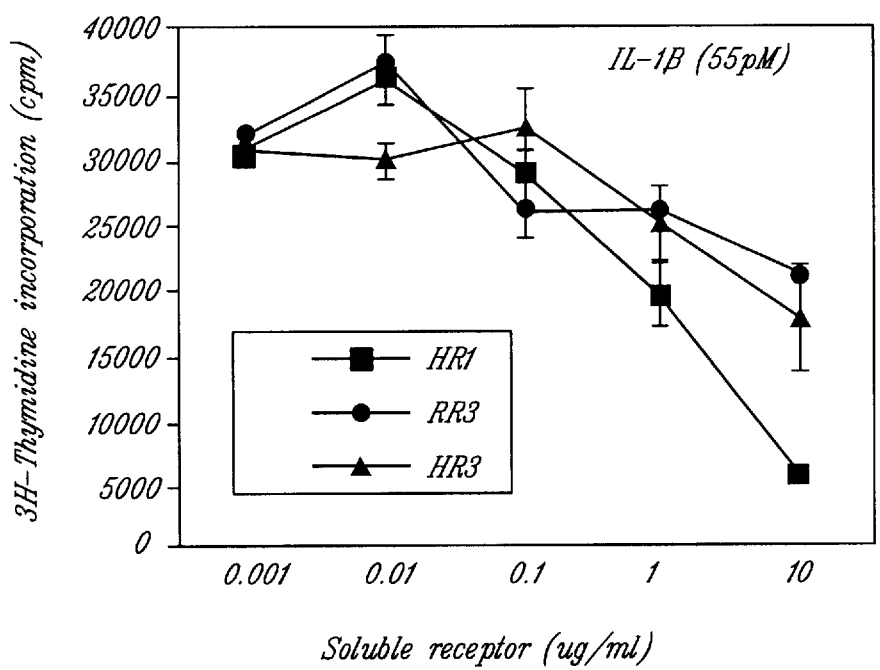

As shown in FIG. 5, both human IL-1 type 3 and rat IL-1 type 3 receptors effectively inhibit thymocyte proliferation in a manner similar to that observed for soluble human type 1 receptor. This result strongly indicates that the type 3 receptor inhibits thymocyte proliferation by binding to the exogenously added IL-1.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated nucleic acid molecule encoding an Interleukin-1 Type 3 receptor, comprising the sequence of nucleotides in Sequence I.D. No. 1, from nucleotide number 129 to nucleotide number 1814.

2. An isolated nucleic acid molecule encoding an Interleukin-1 Type 3 receptor, wherein said molecule encodes a protein having the amino acid sequence of Sequence I.D. No. 2, from amino acid number 1 to amino acid number 562.

3. An isolated nucleic acid molecule encoding an Interleukin-1 Type 3 receptor, comprising the sequence of nucleotides in Sequence I.D. No. 3, from nucleotide number 89 to nucleotide number 1771.

4. An isolated nucleic acid molecule encoding an Interleukin-1 Type 3 receptor, wherein said molecule encodes a protein having the amino acid sequence of Sequence I.D. No. 4, from amino acid number 1 to amino acid number 561.

5. An isolated nucleic acid molecule encoding a soluble Interleukin-1 Type 3 receptor, comprising the sequence of nucleotides in Sequence I.D. No. 1, from nucleotide number 129 to nucleotide number 1136.

6. An isolated nucleic acid molecule encoding a soluble Interleukin-1 Type 3 receptor, wherein said molecule encodes a protein having the amino acid sequence of Sequence I.D. No. 2, from amino acid number 1 to amino acid number 336.

7. An isolated nucleic acid molecule encoding a soluble Interleukin-1 Type 3 receptor, comprising the sequence of nucleotides in Sequence I.D. No. 3, from nucleotide number 89 to nucleotide number 1102.

8. An isolated nucleic acid molecule encoding a soluble Interleukin-1 Type 3 receptor, wherein said molecule encodes a protein having the amino acid sequence of Sequence I.D. No. 4, from amino acid number 1 to amino acid number 338.

9. A recombinant expression vector, comprising a promoter operably linked to a nucleic acid molecule according to any one of claims 1 to 8.

10. A recombinant viral vector capable of directing the expression of a nucleic acid molecule according to any one of claims 1 to 8 wherein said vector is selected from the group consisting of retroviral vectors, adenoviral vectors, and herpes simplex virus vectors.

11. A host cell containing a recombinant vector according to claim 9.

12. An isolated soluble Interleukin-1 Type 3 receptor having the amino acid sequence of Sequence I.D. No. 2, from amino acid number 1 to amino acid number 336.

13. An isolated soluble Interleukin-1 Type 3 receptor having the amino acid sequence of Sequence I.D. No. 4, from amino acid number 1 to amino acid number 338.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
       (A) LENGTH: 1965 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 129..1814

(xi) SEQUENCE DESCRIPTION: SEQ ID NO: 1:

```
CGCCCGCCCA CGGCGGCGGG GAAATACCTA GGCATGGAAG TGGCATGACA GGGCTCGTGT         60

CCCTGTCATA TTTTCCACTC TCCACGAGGT CCTGCGCGCT TCAATCCTGC AGGCAGCCCG        120

GTTTGGGG ATG TGG TCC TTG CTG CTC TGC GGG TTG TCC ATC GCC CTT CCA        170
         Met Trp Ser Leu Leu Leu Cys Gly Leu Ser Ile Ala Leu Pro
           1               5                  10

CTG TCT GTC ACA GCA GAT GGA TGC AAG GAC ATT TTT ATG AAA AAT GAG         218
Leu Ser Val Thr Ala Asp Gly Cys Lys Asp Ile Phe Met Lys Asn Glu
 15              20                  25                  30

ATA CTT TCA GCA AGC CAG CCT TTT GCT TTT AAT TGT ACA TTC CCT CCC         266
Ile Leu Ser Ala Ser Gln Pro Phe Ala Phe Asn Cys Thr Phe Pro Pro
                 35                  40                  45

ATA ACA TCT GGG GAA GTC AGT GTA ACA TGG TAT AAA AAT TCT AGC AAA         314
Ile Thr Ser Gly Glu Val Ser Val Thr Trp Tyr Lys Asn Ser Ser Lys
             50                  55                  60

ATC CCA GTG TCC AAA ATC ATA CAG TCT AGA ATT CAC CAG GAC GAG ACT         362
Ile Pro Val Ser Lys Ile Ile Gln Ser Arg Ile His Gln Asp Glu Thr
 65                  70                  75

TGG ATT TTG TTT CTC CCC ATG GAA TGG GGG GAC TCA GGA GTC TAC CAA         410
Trp Ile Leu Phe Leu Pro Met Glu Trp Gly Asp Ser Gly Val Tyr Gln
         80                  85                  90

TGT GTT ATA AAG GGT AGA GAC AGC TGT CAT AGA ATA CAT GTA AAC CTA         458
Cys Val Ile Lys Gly Arg Asp Ser Cys His Arg Ile His Val Asn Leu
 95                 100                 105                 110

ACT GTT TTT GAA AAA CAT TGG TGT GAC ACT TCC ATA GGT GGT TTA CCA         506
Thr Val Phe Glu Lys His Trp Cys Asp Thr Ser Ile Gly Gly Leu Pro
                115                 120                 125

AAT TTA TCA GAT GAG TAC AAG CAA ATA TTA CAT CTT GGA AAA GAT GAT         554
Asn Leu Ser Asp Glu Tyr Lys Gln Ile Leu His Leu Gly Lys Asp Asp
            130                 135                 140

AGT CTC ACA TGT CAT CTG CAC TTC CCG AAG AGT TGT GTT TTG GGT CCA         602
Ser Leu Thr Cys His Leu His Phe Pro Lys Ser Cys Val Leu Gly Pro
145                 150                 155

ATA AAG TGG TAT AAG GAC TGT AAC GAG ATT AAA GGG GAG CGG TTC ACT         650
Ile Lys Trp Tyr Lys Asp Cys Asn Glu Ile Lys Gly Glu Arg Phe Thr
        160                 165                 170

GTT TTG GAA ACC AGG CTT TTG GTG AGC AAT GTC TCG GCA GAG GAC AGA         698
Val Leu Glu Thr Arg Leu Leu Val Ser Asn Val Ser Ala Glu Asp Arg
175                 180                 185                 190

GGG AAC TAC GCG TGT CAA GCC ATA CTG ACA CAC TCA GGG AAG CAG TAC         746
Gly Asn Tyr Ala Cys Gln Ala Ile Leu Thr His Ser Gly Lys Gln Tyr
                195                 200                 205

GAG GTT TTA AAT GGC ATC ACT GTG AGC ATT ACA GAA AGA GCT GGA TAT         794
Glu Val Leu Asn Gly Ile Thr Val Ser Ile Thr Glu Arg Ala Gly Tyr
```

```
                                        -continued

Glu Val Leu Asn Gly Ile Thr Val Ser Ile Thr Glu Arg Ala Gly Tyr
            210                 215                 220

GGA GGA AGT GTC CCT AAA ATC ATT TAT CCA AAA AAT CAT TCA ATT GAA       842
Gly Gly Ser Val Pro Lys Ile Ile Tyr Pro Lys Asn His Ser Ile Glu
            225                 230                 235

GTA CAG CTT GGT ACC ACT CTG ATT GTG GAC TGC AAT GTA ACA GAC ACC       890
Val Gln Leu Gly Thr Thr Leu Ile Val Asp Cys Asn Val Thr Asp Thr
        240                 245                 250

AAG GAT AAT ACA AAT CTA CGA TGC TGG AGA GTC AAT AAC ACT TTG GTG       938
Lys Asp Asn Thr Asn Leu Arg Cys Trp Arg Val Asn Asn Thr Leu Val
255                 260                 265                 270

GAT GAT TAC TAT GAT GAA TCC AAA CGA ATC AGA GAA GGG GTG GAA ACC       986
Asp Asp Tyr Tyr Asp Glu Ser Lys Arg Ile Arg Glu Gly Val Glu Thr
                275                 280                 285

CAT GTC TCT TTT CGG GAA CAT AAT TTG TAC ACA GTA AAC ATC ACC TTC      1034
His Val Ser Phe Arg Glu His Asn Leu Tyr Thr Val Asn Ile Thr Phe
            290                 295                 300

TTG GAA GTG AAA ATG GAA GAT TAT GGC CTT CCT TTC ATG TGC CAC GCT      1082
Leu Glu Val Lys Met Glu Asp Tyr Gly Leu Pro Phe Met Cys His Ala
            305                 310                 315

GGA GTG TCC ACA GCA TAC ATT ATA TTA CAG CTC CCA GCT CCG GAT TTT      1130
Gly Val Ser Thr Ala Tyr Ile Ile Leu Gln Leu Pro Ala Pro Asp Phe
        320                 325                 330

CGA GCT TAC TTG ATA GGA GGG CTT ATC GCC TTG GTG GCT GTG GCT GTG      1178
Arg Ala Tyr Leu Ile Gly Gly Leu Ile Ala Leu Val Ala Val Ala Val
335                 340                 345                 350

TCT GTT GTG TAC ATA TAC AAC ATT TTT AAG ATC GAC ATT GTT CTT TGG      1226
Ser Val Val Tyr Ile Tyr Asn Ile Phe Lys Ile Asp Ile Val Leu Trp
                355                 360                 365

TAT CGA AGT GCC TTC CAT TCT ACA GAG ACC ATA GTA GAT GGG AAG CTG      1274
Tyr Arg Ser Ala Phe His Ser Thr Glu Thr Ile Val Asp Gly Lys Leu
            370                 375                 380

TAT GAC GCC TAT GTC TTA TAC CCC AAG CCC CAC AAG GAA AGC CAG AGG      1322
Tyr Asp Ala Tyr Val Leu Tyr Pro Lys Pro His Lys Glu Ser Gln Arg
            385                 390                 395

CAT GCC GTG GAT GCC CTG GTG TTG AAT ATC CTG CCC GAG GTG TTG GAG      1370
His Ala Val Asp Ala Leu Val Leu Asn Ile Leu Pro Glu Val Leu Glu
        400                 405                 410

AGA CAA TGT GGA TAT AAG TTG TTT ATA TTC GGC AGA GAT GAA TTC CCT      1418
Arg Gln Cys Gly Tyr Lys Leu Phe Ile Phe Gly Arg Asp Glu Phe Pro
415                 420                 425                 430

GGA CAA GCC GTG GCC AAT GTC ATC GAT GAA AAC GTT AAG CTG TGC AGG      1466
Gly Gln Ala Val Ala Asn Val Ile Asp Glu Asn Val Lys Leu Cys Arg
                435                 440                 445

AGG CTG ATT GTC ATT GTG GTC CCC GAA TCG CTG GGC TTT GGC CTG TTG      1514
Arg Leu Ile Val Ile Val Val Pro Glu Ser Leu Gly Phe Gly Leu Leu
            450                 455                 460

AAG AAC CTG TCA GAA GAA CAA ATC GCG GTC TAC AGT GCC CTG ATC CAG      1562
Lys Asn Leu Ser Glu Glu Gln Ile Ala Val Tyr Ser Ala Leu Ile Gln
            465                 470                 475

GAC GGG ATG AAG GTT ATT CTC ATT GAG CTG GAG AAA ATC GAG GAC TAC      1610
Asp Gly Met Lys Val Ile Leu Ile Glu Leu Glu Lys Ile Glu Asp Tyr
        480                 485                 490

ACA GTC ATG CCA GAG TCA ATT CAG TAC ATC AAA CAG AAG CAT GGT GCC      1658
Thr Val Met Pro Glu Ser Ile Gln Tyr Ile Lys Gln Lys His Gly Ala
495                 500                 505                 510

ATC CGG TGG CAT GGG GAC TTC ACG GAG CAG TCA CAG TGT ATG AAG ACC      1706
Ile Arg Trp His Gly Asp Phe Thr Glu Gln Ser Gln Cys Met Lys Thr
                515                 520                 525
```

-continued

```
AAG TTT TGG AAG ACA GTG AGA TAC CAC ATG CCG CCC AGA AGG TGT CGG      1754
Lys Phe Trp Lys Thr Val Arg Tyr His Met Pro Pro Arg Arg Cys Arg
        530                 535                 540

CCG TTT CTC CGG TCC ACG TGC CGC AGC ACA CAC CTC TGT ACC GCA CCG      1802
Pro Phe Leu Arg Ser Thr Cys Arg Ser Thr His Leu Cys Thr Ala Pro
        545                 550                 555

CAG GCC CAG AAC TAGGCTCAAG AAGAAAGAAG TGTACTCTCA CGACTGGCTA          1854
Gln Ala Gln Asn
        560

AGACTTGCTG GACTGACACC TATGGCTGGA AGATGACTTG TTTTGCTCCA TGTCTCCTCA    1914

TTCCTACACC TATTTTCTGC TGCAGGATGA GGCTAGGGTT AGCATTCTAG A             1965
```

(2) INFORMATION FOR SEQ ID NO: 2:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Trp Ser Leu Leu Leu Cys Gly Leu Ser Ile Ala Leu Pro Leu Ser
 1               5                  10                  15

Val Thr Ala Asp Gly Cys Lys Asp Ile Phe Met Lys Asn Glu Ile Leu
             20                  25                  30

Ser Ala Ser Gln Pro Phe Ala Phe Asn Cys Thr Phe Pro Pro Ile Thr
         35                  40                  45

Ser Gly Glu Val Ser Val Thr Trp Tyr Lys Asn Ser Ser Lys Ile Pro
     50                  55                  60

Val Ser Lys Ile Ile Gln Ser Arg Ile His Gln Asp Glu Thr Trp Ile
 65                  70                  75                  80

Leu Phe Leu Pro Met Glu Trp Gly Asp Ser Gly Val Tyr Gln Cys Val
                 85                  90                  95

Ile Lys Gly Arg Asp Ser Cys His Arg Ile His Val Asn Leu Thr Val
            100                 105                 110

Phe Glu Lys His Trp Cys Asp Thr Ser Ile Gly Gly Leu Pro Asn Leu
        115                 120                 125

Ser Asp Glu Tyr Lys Gln Ile Leu His Leu Gly Lys Asp Asp Ser Leu
    130                 135                 140

Thr Cys His Leu His Phe Pro Lys Ser Cys Val Leu Gly Pro Ile Lys
145                 150                 155                 160

Trp Tyr Lys Asp Cys Asn Glu Ile Lys Gly Glu Arg Phe Thr Val Leu
                165                 170                 175

Glu Thr Arg Leu Leu Val Ser Asn Val Ser Ala Glu Asp Arg Gly Asn
            180                 185                 190

Tyr Ala Cys Gln Ala Ile Leu Thr His Ser Gly Lys Gln Tyr Glu Val
        195                 200                 205

Leu Asn Gly Ile Thr Val Ser Ile Thr Glu Arg Ala Gly Tyr Gly Gly
    210                 215                 220

Ser Val Pro Lys Ile Ile Tyr Pro Lys Asn His Ser Ile Glu Val Gln
225                 230                 235                 240

Leu Gly Thr Thr Leu Ile Val Asp Cys Asn Val Thr Asp Thr Lys Asp
                245                 250                 255

Asn Thr Asn Leu Arg Cys Trp Arg Val Asn Asn Thr Leu Val Asp Asp
            260                 265                 270
```

```
Tyr Tyr Asp Glu Ser Lys Arg Ile Arg Glu Gly Val Glu Thr His Val
        275                 280                 285

Ser Phe Arg Glu His Asn Leu Tyr Thr Val Asn Ile Thr Phe Leu Glu
        290                 295                 300

Val Lys Met Glu Asp Tyr Gly Leu Pro Phe Met Cys His Ala Gly Val
305                 310                 315                 320

Ser Thr Ala Tyr Ile Ile Leu Gln Leu Pro Ala Pro Asp Phe Arg Ala
                325                 330                 335

Tyr Leu Ile Gly Gly Leu Ile Ala Leu Val Ala Val Ala Val Ser Val
                340                 345                 350

Val Tyr Ile Tyr Asn Ile Phe Lys Ile Asp Ile Val Leu Trp Tyr Arg
                355                 360                 365

Ser Ala Phe His Ser Thr Glu Thr Ile Val Asp Gly Lys Leu Tyr Asp
        370                 375                 380

Ala Tyr Val Leu Tyr Pro Lys Pro His Lys Glu Ser Gln Arg His Ala
385                 390                 395                 400

Val Asp Ala Leu Val Leu Asn Ile Leu Pro Glu Val Leu Glu Arg Gln
                405                 410                 415

Cys Gly Tyr Lys Leu Phe Ile Phe Gly Arg Asp Glu Phe Pro Gly Gln
                420                 425                 430

Ala Val Ala Asn Val Ile Asp Glu Asn Val Lys Leu Cys Arg Arg Leu
                435                 440                 445

Ile Val Ile Val Val Pro Glu Ser Leu Gly Phe Gly Leu Leu Lys Asn
450                 455                 460

Leu Ser Glu Glu Gln Ile Ala Val Tyr Ser Ala Leu Ile Gln Asp Gly
465                 470                 475                 480

Met Lys Val Ile Leu Ile Glu Leu Glu Lys Ile Glu Asp Tyr Thr Val
                485                 490                 495

Met Pro Glu Ser Ile Gln Tyr Ile Lys Gln Lys His Gly Ala Ile Arg
                500                 505                 510

Trp His Gly Asp Phe Thr Glu Gln Ser Gln Cys Met Lys Thr Lys Phe
                515                 520                 525

Trp Lys Thr Val Arg Tyr His Met Pro Pro Arg Arg Cys Arg Pro Phe
530                 535                 540

Leu Arg Ser Thr Cys Arg Ser Thr His Leu Cys Thr Ala Pro Gln Ala
545                 550                 555                 560

Gln Asn (2) INFORMATION FOR SEQ ID NO: 3:

(i) SEQUENCE CHARACTERISTICS:
        (A) LENGTH: 2044 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 89..1771

(xi) SEQUENCE DESCRIPTION: SEQ ID NO: 3:

CCGGCTGGCC TAGGATCAGG CAAGAAAAGG CTGAACGCCT TTCTAAGGAC GGACTCTTTC      60

TGTACAGCTC CACTTGGGGA AGCCCGAA ATG GGG ATG CCA CCC TTG CTC TTC        112
                              Met Gly Met Pro Pro Leu Leu Phe
                               1               5

TGT TGG GTG TCT TTC GTG CTT CCA CTT TTT GTG GCA GCA GGT AAC TGT       160
Cys Trp Val Ser Phe Val Leu Pro Leu Phe Val Ala Ala Gly Asn Cys
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 10  |     |     |     |     | 15  |     |     |     |     | 20  |     |     |     |
| ACT | GAT | GTC | TAT | ATG | CAC | CAT | GAG | ATG | ATT | TCA | GAG | GGC | CAG | CCT | TTC | 208 |
| Thr | Asp | Val | Tyr | Met | His | His | Glu | Met | Ile | Ser | Glu | Gly | Gln | Pro | Phe |
| 25  |     |     |     |     | 30  |     |     |     |     | 35  |     |     |     |     | 40  |
| CCC | TTC | AAC | TGC | ACA | TAC | CCT | CCA | GTA | ACA | AAC | GGG | GCA | GTG | AAT | CTG | 256 |
| Pro | Phe | Asn | Cys | Thr | Tyr | Pro | Pro | Val | Thr | Asn | Gly | Ala | Val | Asn | Leu |
|     |     |     |     | 45  |     |     |     |     | 50  |     |     |     |     | 55  |     |
| ACA | TGG | CAT | AGA | ACA | CCC | AGT | AAG | AGC | CCA | ATC | TCC | ATC | AAC | AGA | CAC | 304 |
| Thr | Trp | His | Arg | Thr | Pro | Ser | Lys | Ser | Pro | Ile | Ser | Ile | Asn | Arg | His |
|     |     |     | 60  |     |     |     |     | 65  |     |     |     |     | 70  |     |     |
| GTT | AGA | ATT | CAC | CAG | GAC | CAG | TCC | TGG | ATT | TTG | TTT | CTT | CCG | TTG | GCA | 352 |
| Val | Arg | Ile | His | Gln | Asp | Gln | Ser | Trp | Ile | Leu | Phe | Leu | Pro | Leu | Ala |
|     |     | 75  |     |     |     |     | 80  |     |     |     |     | 85  |     |     |     |
| TTG | GAG | GAC | TCA | GGC | ATC | TAT | CAA | TGT | GTT | ATA | AAG | GAT | GCC | CAC | AGC | 400 |
| Leu | Glu | Asp | Ser | Gly | Ile | Tyr | Gln | Cys | Val | Ile | Lys | Asp | Ala | His | Ser |
|     | 90  |     |     |     |     | 95  |     |     |     |     | 100 |     |     |     |     |
| TGT | TAC | CGA | ATA | GCT | ATA | AAC | CTA | ACC | GTT | TTT | AGA | AAA | CAC | TGG | TGC | 448 |
| Cys | Tyr | Arg | Ile | Ala | Ile | Asn | Leu | Thr | Val | Phe | Arg | Lys | His | Trp | Cys |
| 105 |     |     |     |     | 110 |     |     |     |     | 115 |     |     |     |     | 120 |
| GAC | TCT | TCC | AAC | GAA | GAG | AGT | TCC | ATA | AAT | TCC | TCA | GAT | GAG | TAC | CAG | 496 |
| Asp | Ser | Ser | Asn | Glu | Glu | Ser | Ser | Ile | Asn | Ser | Ser | Asp | Glu | Tyr | Gln |
|     |     |     |     | 125 |     |     |     |     | 130 |     |     |     |     | 135 |     |
| CAA | TGG | TTA | CCC | ATA | GGA | AAA | TCG | GGC | AGT | CTG | ACG | TGC | CAT | CTC | TAC | 544 |
| Gln | Trp | Leu | Pro | Ile | Gly | Lys | Ser | Gly | Ser | Leu | Thr | Cys | His | Leu | Tyr |
|     |     |     | 140 |     |     |     |     | 145 |     |     |     |     | 150 |     |     |
| TTC | CCA | GAG | AGC | TGT | GTT | TTG | GAT | TCA | ATA | AAG | TGG | TAT | AAG | GGT | TGT | 592 |
| Phe | Pro | Glu | Ser | Cys | Val | Leu | Asp | Ser | Ile | Lys | Trp | Tyr | Lys | Gly | Cys |
|     |     | 155 |     |     |     |     | 160 |     |     |     |     | 165 |     |     |     |
| GAA | GAG | ATT | AAA | GTG | AGC | AAG | AAG | TTT | TGC | CCT | ACA | GGA | ACA | AAG | CTT | 640 |
| Glu | Glu | Ile | Lys | Val | Ser | Lys | Lys | Phe | Cys | Pro | Thr | Gly | Thr | Lys | Leu |
|     | 170 |     |     |     |     | 175 |     |     |     |     | 180 |     |     |     |     |
| CTT | GTT | AAC | AAC | ATC | GAC | GTG | GAG | GAT | AGT | GGG | AGC | TAT | GCA | TGC | TCA | 688 |
| Leu | Val | Asn | Asn | Ile | Asp | Val | Glu | Asp | Ser | Gly | Ser | Tyr | Ala | Cys | Ser |
| 185 |     |     |     |     | 190 |     |     |     |     | 195 |     |     |     |     | 200 |
| GCC | AGA | CTG | ACA | CAC | TTG | GGG | AGA | ATC | TTC | ACG | GTT | AGA | AAC | TAC | ATT | 736 |
| Ala | Arg | Leu | Thr | His | Leu | Gly | Arg | Ile | Phe | Thr | Val | Arg | Asn | Tyr | Ile |
|     |     |     |     | 205 |     |     |     |     | 210 |     |     |     |     | 215 |     |
| GCT | GTG | AAT | ACC | AAG | GAA | GTT | GGG | TCT | GGA | GGA | AGG | ATC | CCT | AAC | ATC | 784 |
| Ala | Val | Asn | Thr | Lys | Glu | Val | Gly | Ser | Gly | Gly | Arg | Ile | Pro | Asn | Ile |
|     |     |     | 220 |     |     |     |     | 225 |     |     |     |     | 230 |     |     |
| ACG | TAT | CCA | AAA | AAC | AAC | TCC | ATT | GAA | GTT | CAA | CTT | GGC | TCC | ACC | CTC | 832 |
| Thr | Tyr | Pro | Lys | Asn | Asn | Ser | Ile | Glu | Val | Gln | Leu | Gly | Ser | Thr | Leu |
|     |     | 235 |     |     |     |     | 240 |     |     |     |     | 245 |     |     |     |
| ATT | GTG | GAC | TGC | AAT | ATA | ACA | GAC | ACG | AAG | GAG | AAT | ACG | AAC | CTC | AGA | 880 |
| Ile | Val | Asp | Cys | Asn | Ile | Thr | Asp | Thr | Lys | Glu | Asn | Thr | Asn | Leu | Arg |
|     | 250 |     |     |     |     | 255 |     |     |     |     | 260 |     |     |     |     |
| TGC | TGG | CGA | GTT | AAC | AAC | ACC | CTG | GTG | GAC | GAT | TAC | TAC | AAC | GAC | TTC | 928 |
| Cys | Trp | Arg | Val | Asn | Asn | Thr | Leu | Val | Asp | Asp | Tyr | Tyr | Asn | Asp | Phe |
| 265 |     |     |     | 270 |     |     |     |     | 275 |     |     |     |     | 280 |     |
| AAA | CGC | ATC | CAG | GAA | GGA | ATC | GAA | ACC | AAT | CTG | TCT | CTG | AGG | AAT | CAC | 976 |
| Lys | Arg | Ile | Gln | Glu | Gly | Ile | Glu | Thr | Asn | Leu | Ser | Leu | Arg | Asn | His |
|     |     |     |     | 285 |     |     |     |     | 290 |     |     |     |     | 295 |     |
| ATT | CTG | TAC | ACA | GTG | AAC | ATA | ACA | TTC | TTA | GAA | GTG | AAA | ATG | GAG | GAC | 1024 |
| Ile | Leu | Tyr | Thr | Val | Asn | Ile | Thr | Phe | Leu | Glu | Val | Lys | Met | Glu | Asp |
|     |     |     | 300 |     |     |     |     | 305 |     |     |     |     | 310 |     |     |
| TAC | GGC | CAT | CCT | TTC | ACA | TGC | CAC | GCT | GCG | GTG | TCC | GCA | GCC | TAC | ATC | 1072 |
| Tyr | Gly | His | Pro | Phe | Thr | Cys | His | Ala | Ala | Val | Ser | Ala | Ala | Tyr | Ile |
|     |     | 315 |     |     |     |     | 320 |     |     |     |     | 325 |     |     |     |
| ATT | CTG | AAA | CGC | CCA | GCT | CCA | GAC | TTC | CGG | GCT | TAC | CTC | ATA | GGA | GGT | 1120 |

```
Ile Leu Lys Arg Pro Ala Pro Asp Phe Arg Ala Tyr Leu Ile Gly Gly
    330                 335                 340

CTC ATG GCT TTC CTA CTT CTG GCC GTG TCC ATT CTG TAC ATC TAC AAC     1168
Leu Met Ala Phe Leu Leu Leu Ala Val Ser Ile Leu Tyr Ile Tyr Asn
345                 350                 355                 360

ACC TTT AAG GTC GAC ATC GTG CTT TGG TAT AGG AGT ACC TTC CAC ACT     1216
Thr Phe Lys Val Asp Ile Val Leu Trp Tyr Arg Ser Thr Phe His Thr
                365                 370                 375

GCC CAG GCT CCA GAT GAC GAG AAG CTG TAT GAT GCC TAT GTC TTA TAC     1264
Ala Gln Ala Pro Asp Asp Glu Lys Leu Tyr Asp Ala Tyr Val Leu Tyr
            380                 385                 390

CCC AAG TAC CCA AGA GAA AGC CAG GGC CAT GAT GTG GAC ACA CTG GTG     1312
Pro Lys Tyr Pro Arg Glu Ser Gln Gly His Asp Val Asp Thr Leu Val
        395                 400                 405

TTG AAG ATC TTG CCC GAG GTG CTG GAG AAA CAG TGT GGA TAT AAG TTA     1360
Leu Lys Ile Leu Pro Glu Val Leu Glu Lys Gln Cys Gly Tyr Lys Leu
    410                 415                 420

TTC ATA TTT GGC AGG GAT GAA TTC CCT GGA CAA GCT GTG GCC AGC GTC     1408
Phe Ile Phe Gly Arg Asp Glu Phe Pro Gly Gln Ala Val Ala Ser Val
425                 430                 435                 440

ATT GAT GAA AAC ATT AAG CTG TGT AGG AGG CTG ATG GTC CTC GTG GCA     1456
Ile Asp Glu Asn Ile Lys Leu Cys Arg Arg Leu Met Val Leu Val Ala
                445                 450                 455

CCA GAG ACA TCC AGC TTC AGC TTT CTG AAG AAC TTG ACT GAA GAA CAA     1504
Pro Glu Thr Ser Ser Phe Ser Phe Leu Lys Asn Leu Thr Glu Glu Gln
            460                 465                 470

ATC GCT GTC TAC AAT GCC CTC GTC CAG GAC GGC ATG AAG GTC ATT CTG     1552
Ile Ala Val Tyr Asn Ala Leu Val Gln Asp Gly Met Lys Val Ile Leu
        475                 480                 485

ATT GAA CTG GAG AGA GTC AAG GAC TAC AGC ACC ATG CCC GAG TCC ATT     1600
Ile Glu Leu Glu Arg Val Lys Asp Tyr Ser Thr Met Pro Glu Ser Ile
    490                 495                 500

CAG TAC ATC CGA CAG AAG CAC GGG GCC ATC CAG TGG GAT GGG GAC TTC     1648
Gln Tyr Ile Arg Gln Lys His Gly Ala Ile Gln Trp Asp Gly Asp Phe
505                 510                 515                 520

ACA GAG CAG GCA CAG TGC GCC AAG ACG AAA TTC TGG AAG AAA GTG AGA     1696
Thr Glu Gln Ala Gln Cys Ala Lys Thr Lys Phe Trp Lys Lys Val Arg
                525                 530                 535

TAT CAT ATG CCA CCC AGG AGG TAC CCG GCA TCT CCC CCC GTC CAG CTG     1744
Tyr His Met Pro Pro Arg Arg Tyr Pro Ala Ser Pro Pro Val Gln Leu
            540                 545                 550

CTA GGA CAC ACA CCC CGC ATA CCA GGC TAGTGCAGTG CCACCGCCAC           1791
Leu Gly His Thr Pro Arg Ile Pro Gly
        555                 560

GGGGCTCATA ACTCCTTAAG AGCGGTTAGT GTGTGGTGGC TCGCACTACA ACCTCTCTGG   1851

ATCATCTACC CCCGTAGCTT GCTCTTTTGT GCTTGTGAGC GACCTCGTCC TTAGCCACGT   1911

CATATTTTGA TTTTTTGTTT GTTTTGTTTG TTTGTTGTAT GCTTTTAGTC ATAGCTGATT   1971

CGTACTACTC CTGTTTGCTT CATGGTTCCT GAATCCCAGA GACTCCCTGA GCATGGGTGG   2031

CTATCATGTT GGG                                                     2044

(2) INFORMATION FOR SEQ ID NO: 4:

(i) SEQUENCE CHARACTERISTICS:
        (A) LENGTH: 561 amino acids
        (B) TYPE: amino acid
        (D) TOPOLOGY: linear (ii) MOLECULE TYPE: protein
```

(xi) SEQUENCE DESCRIPTION: SEQ ID NO: 4:

```
Met Gly Met Pro Pro Leu Leu Phe Cys Trp Val Ser Phe Val Leu Pro
 1               5                  10                  15

Leu Phe Val Ala Ala Gly Asn Cys Thr Asp Val Tyr Met His His Glu
             20                  25                  30

Met Ile Ser Glu Gly Gln Pro Phe Pro Phe Asn Cys Thr Tyr Pro Pro
         35                  40                  45

Val Thr Asn Gly Ala Val Asn Leu Thr Trp His Arg Thr Pro Ser Lys
     50                  55                  60

Ser Pro Ile Ser Ile Asn Arg His Val Arg Ile His Gln Asp Gln Ser
 65                  70                  75                  80

Trp Ile Leu Phe Leu Pro Leu Ala Leu Glu Asp Ser Gly Ile Tyr Gln
                 85                  90                  95

Cys Val Ile Lys Asp Ala His Ser Cys Tyr Arg Ile Ala Ile Asn Leu
                100                 105                 110

Thr Val Phe Arg Lys His Trp Cys Asp Ser Ser Asn Glu Glu Ser Ser
            115                 120                 125

Ile Asn Ser Ser Asp Glu Tyr Gln Gln Trp Leu Pro Ile Gly Lys Ser
130                 135                 140

Gly Ser Leu Thr Cys His Leu Tyr Phe Pro Glu Ser Cys Val Leu Asp
145                 150                 155                 160

Ser Ile Lys Trp Tyr Lys Gly Cys Glu Ile Lys Val Ser Lys Lys
                165                 170                 175

Phe Cys Pro Thr Gly Thr Lys Leu Leu Val Asn Asn Ile Asp Val Glu
                180                 185                 190

Asp Ser Gly Ser Tyr Ala Cys Ser Ala Arg Leu Thr His Leu Gly Arg
            195                 200                 205

Ile Phe Thr Val Arg Asn Tyr Ile Ala Val Asn Thr Lys Glu Val Gly
        210                 215                 220

Ser Gly Gly Arg Ile Pro Asn Ile Thr Tyr Pro Lys Asn Asn Ser Ile
225                 230                 235                 240

Glu Val Gln Leu Gly Ser Thr Leu Ile Val Asp Cys Asn Ile Thr Asp
                245                 250                 255

Thr Lys Glu Asn Thr Asn Leu Arg Cys Trp Arg Val Asn Asn Thr Leu
            260                 265                 270

Val Asp Asp Tyr Tyr Asn Asp Phe Lys Arg Ile Gln Glu Gly Ile Glu
        275                 280                 285

Thr Asn Leu Ser Leu Arg Asn His Ile Leu Tyr Thr Val Asn Ile Thr
    290                 295                 300

Phe Leu Glu Val Lys Met Glu Asp Tyr Gly His Pro Phe Thr Cys His
305                 310                 315                 320

Ala Ala Val Ser Ala Ala Tyr Ile Ile Leu Lys Arg Pro Ala Pro Asp
                325                 330                 335

Phe Arg Ala Tyr Leu Ile Gly Gly Leu Met Ala Phe Leu Leu Leu Ala
            340                 345                 350

Val Ser Ile Leu Tyr Ile Tyr Asn Thr Phe Lys Val Asp Ile Val Leu
        355                 360                 365

Trp Tyr Arg Ser Thr Phe His Thr Ala Gln Ala Pro Asp Asp Glu Lys
    370                 375                 380

Leu Tyr Asp Ala Tyr Val Leu Tyr Pro Lys Tyr Pro Arg Glu Ser Gln
385                 390                 395                 400

Gly His Asp Val Asp Thr Leu Val Leu Lys Ile Leu Pro Glu Val Leu
                405                 410                 415
```

Glu Lys Gln Cys Gly Tyr Lys Leu Phe Ile Phe Gly Arg Asp Glu Phe
             420                 425                 430

Pro Gly Gln Ala Val Ala Ser Val Ile Asp Glu Asn Ile Lys Leu Cys
             435                 440                 445

Arg Arg Leu Met Val Leu Val Ala Pro Glu Thr Ser Ser Phe Ser Phe
             450                 455                 460

Leu Lys Asn Leu Thr Glu Glu Gln Ile Ala Val Tyr Asn Ala Leu Val
465                 470                 475                 480

Gln Asp Gly Met Lys Val Ile Leu Ile Glu Leu Glu Arg Val Lys Asp
             485                 490                 495

Tyr Ser Thr Met Pro Glu Ser Ile Gln Tyr Ile Arg Gln Lys His Gly
             500                 505                 510

Ala Ile Gln Trp Asp Gly Asp Phe Thr Glu Gln Ala Gln Cys Ala Lys
             515                 520                 525

Thr Lys Phe Trp Lys Lys Val Arg Tyr His Met Pro Pro Arg Arg Tyr
             530                 535                 540

Pro Ala Ser Pro Pro Val Gln Leu Leu Gly His Thr Pro Arg Ile Pro
545                 550                 555                 560

Gly (2) INFORMATION FOR SEQ ID NO: 5:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 5:

Asp Tyr Lys Asp Asp Asp Asp Lys
1               5

(2) INFORMATION FOR SEQ ID NO: 6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 6:

CTTCAACTGC ACATACCCTC CAGTAACAAA CGGGGCAGTG AATCTGACAT        50

(2) INFORMATION FOR SEQ ID NO: 7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO: 7:

CCTCCCATAA CATCTGGGGA AGTCAGTGTA ACATGGTATA AAAATTCTAG C       51

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 8:

```
CCTACTCGAG ATGTGGTCCT TGCTGCTC                                      28

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 9:

ATGCGCGGCC GCCTATCGAA AATCCGGAGC TGG                                 33
```